United States Patent [19]
Bernier et al.

[11] Patent Number: 6,096,840
[45] Date of Patent: *Aug. 1, 2000

[54] GAS PHASE POLYMERIZATION PROCESS

[75] Inventors: Robert Joseph Noel Bernier, Flemington; Robert Lorenz Boysen, Lebanon, both of N.J.; Robert Cecil Brown, Danbury, Conn.; Mark Gregory Goode, Hurricane, W. Va.; John Henry Moorhouse, Kendall Park, N.J.; Robert Darrell Olson, Charleston, W. Va.; Leonard Sebastian Scarola, Basking Ridge, N.J.; Thomas Edward Spriggs, Cross Lanes, W. Va.; Duan-Fan Wang, Somerville; Gary Harry Williams, Flemington, both of N.J.

[73] Assignee: Union Carbide Chemicals & Plastics Technology Corporation, Danbury, Conn.

[ * ] Notice: This patent is subject to a terminal disclaimer.

[21] Appl. No.: 09/179,218

[22] Filed: Oct. 27, 1998

Related U.S. Application Data

[63] Continuation of application No. 08/510,375, Aug. 2, 1995, Pat. No. 5,834,571, which is a continuation-in-part of application No. 08/284,797, Aug. 2, 1994, Pat. No. 5,453,471.

[51] Int. Cl.[7] ..................................................... C08F 2/00
[52] U.S. Cl. ................................ 526/68; 526/69; 526/70; 526/74; 526/88; 526/901
[58] Field of Search .................................. 526/68, 69, 70, 526/74, 170, 901, 88

[56] References Cited

U.S. PATENT DOCUMENTS

| | | | |
|---|---|---|---|
| 3,254,070 | 5/1966 | Roelen | 260/94.9 |
| 3,256,263 | 6/1966 | Wisseroth et al. | 260/94.9 |
| 3,298,792 | 1/1967 | Di Drusco | 23/284 |
| 3,300,457 | 1/1967 | Schmid et al. | 260/88.2 |
| 3,652,527 | 3/1972 | Trieschmann et al. | 260/93.7 |
| 3,779,712 | 12/1973 | Calvert et al. | 23/288 E |
| 4,012,573 | 3/1977 | Trieschmann et al. | 526/68 |
| 4,379,758 | 4/1983 | Wagner et al. | 252/429 B |
| 4,383,095 | 5/1983 | Goeke et al. | 526/88 |
| 4,543,399 | 9/1985 | Jenkins, III et al. | 526/70 |
| 4,588,790 | 5/1986 | Jenkins, III et al. | 526/70 |
| 4,803,251 | 2/1989 | Goode et al. | 526/74 |
| 4,876,320 | 10/1989 | Fulks et al. | 526/62 |
| 4,933,149 | 6/1990 | Rhee et al. | 422/131 |
| 4,981,929 | 1/1991 | Hussein et al. | 526/125 |
| 4,994,534 | 2/1991 | Rhee et al. | 526/88 |
| 5,200,477 | 4/1993 | Baker et al. | 526/74 |
| 5,352,749 | 10/1994 | DeChellis et al. | 526/68 |
| 5,405,922 | 4/1995 | DeChellis et al. | 526/68 |
| 5,436,304 | 7/1995 | Griffin et al. | 526/68 |

FOREIGN PATENT DOCUMENTS 56-4608    1/1981   Japan .

*Primary Examiner*—David W. Wu
*Assistant Examiner*—Roberto Rabago
*Attorney, Agent, or Firm*—N. L. Balmer

[57] ABSTRACT

A process for producing polymer in a gas phase reactor by introducing a stream of monomer and gas into a polymerization zone while providing at least one liquid component in the polymerization zone.

14 Claims, 1 Drawing Sheet

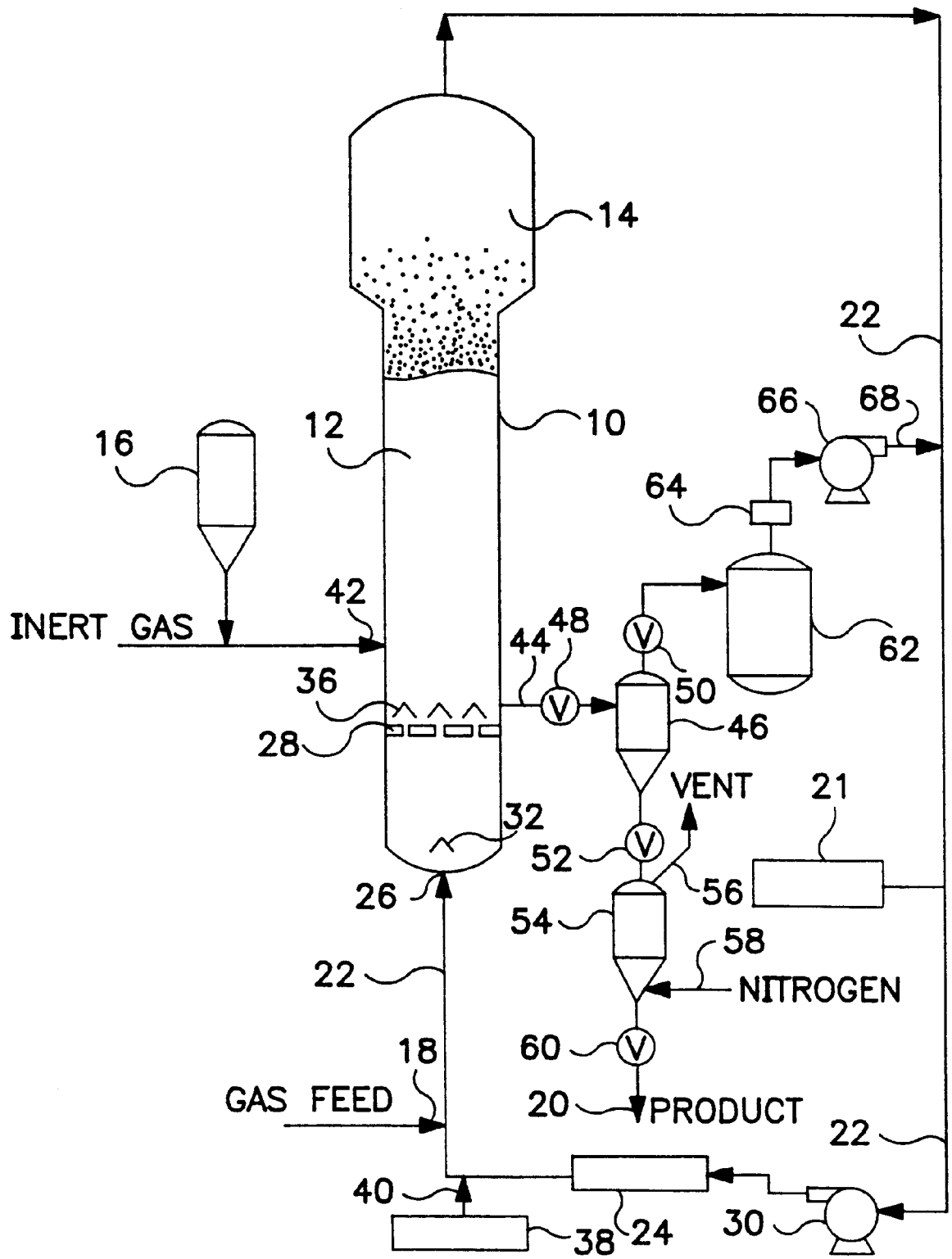

GAS PHASE POLYMERIZATION PROCESS

This application is a continuation of U.S. application Ser. No. 08/510,375, filed Aug. 2, 1995, now U.S. Pat. No. 5,834,571, which in turn is a continuation-in-part application of prior U.S. application Ser. No. 284,797, filed Aug. 2, 1994 now U.S. Pat. No. 5,453,471. Other related patent applications include U.S. applications Ser. Nos. 08/913,310 filed Sep. 16, 1997, and pending Ser. No. 08/930,590 filed Sep. 16, 1997, and provisional patent applications 60/001364, 60/001,366 and 60/001,385 filed on Jul. 21, 1995.

FIELD OF THE INVENTION

This invention relates to a new gas phase polymerization process using liquid in an otherwise gas-phase process.

BACKGROUND OF THE INVENTION

The discovery of gas-phase fluidized bed and stirred reactor processes for the production of polymers, especially polyolefin polymers, made it possible to produce a wide variety of new polymers with highly desirable and improved properties. These gas-phase processes, especially the gas fluidized bed process, provided a means for producing polymers with a drastic reduction in capital investment expense and dramatic savings in energy usage and operating costs as compared to other then conventional polymerization processes.

In a conventional gas fluidized bed process a gaseous stream containing one or more monomers is passed into a fluidized bed reactor containing a bed of growing polymer particles in a polymerization zone, while continuously or intermittently introducing a polymerization catalyst into the polymerization zone. The desired polymer product is withdrawn from the polymerization zone, degassed, stabilized and packaged for shipment, all by well known techniques. Most polymerization reactions, e.g., polymerization of olefins, are exothermic, and substantial heat is generated in the polymerization zone which must be removed to prevent the polymer particles from overheating and fusing together. This is accomplished by continuously removing unreacted hot gases from the polymerization zone and replacing them with cooler gases. The hot gases removed from the polymerization zone are compressed, cooled in a heat exchanger, supplemented by additional amounts of monomer to replace monomer polymerized and removed from the reaction zone and then recycled into the bottom of the reactor. Cooling of the recycled gases is accomplished in one or more heat exchanger stages. The sequence of compression and cooling is a matter of design choice but it is usually preferable to provide for compression of the hot gases prior to cooling. The rate of gas flow into and through the reactor is maintained at a level such that the bed of polymer particles is maintained in a fluidized condition. The production of polymer in a stirred bed reactor is very similar, differing primarily in the use of mechanical stirring means to assist an upwardly flowing stream of gases in maintaining the polymer bed in a fluidized condition.

Conventional gas phase fluidized bed resin production is very well known in the art as shown, for example, by the disclosures appearing in U.S. Pat. Nos. 4,379,758, 4,383,095 and 4,876,320, which are incorporated herein be reference.

The production of polymeric substances in gas phase stirred reactors is also well known in the art as exemplified by the process and equipment descriptions appearing in U.S. Pat. No. 3,256,263.

For many years it was erroneously believed that to allow liquid of any kind to enter into the polymerization region of a gas phase reactor would inevitably lead to agglomeration of resin particles, formation of large polymer chunks and ultimately complete reactor shut-down. This concern caused gas phase polymer producers to carefully avoid cooling the recycle gas stream entering the reactor to a temperature below the condensation temperature of any of the monomers employed in the polymerization reaction.

Comonomers such as hexene-1, 4-methyl pentene and octene-1, are particularly valuable for producing ethylene copolymers. These higher alpha olefins have relatively high condensation temperatures. Due to the apprehension that liquid monomers in the polymerization zone would lead to agglomeration, chunking and ultimately shut down the reactor, production rates which depend upon the rate at which heat is removed from the polymerization zone, were severely constrained by the perceived need to maintain the temperature of the cycle gas stream entering the reactor at temperature safely above the condensation temperature of the highest boiling monomer present in the cycle gas stream.

Even in the case of polymerization reactions conducted in fluidized, stirred reactors, care was exercised to maintain the resin bed temperature above the condensation temperature of the recycle gas stream components.

To maximum heat removal it was not unusual to spray or inject liquid or onto the polymer bed where it would immediately flash into a gaseous state by exposure to the hotter recycle gas stream. A limited amount of additional cooling was achieved by this technique by the Joule-Thompson effect but without ever cooling the recycle gas stream to a level where condensation might occur. This approach typically involved the laborious and energy wasting approach of separately cooling a portion of the cycle gas stream to obtain liquid monomer for storage and subsequent separate introduction into or onto the polymerization bed. Examples of this procedure are found in U.S. Pat. Nos. 3,254,070; 3,300,457; 3,652,527 and 4,012,573.

It was discovered later, contrary to the long held belief that the presence of liquid in the cycle gas stream would lead to agglomeration and reactor shut-down, that it is indeed possible to cool the entire cycle gas stream to a temperature where condensation of significant amounts of monomer would occur without the expected dire results when these liquids were introduced into the reactor substantially in temperature equilibrium with the recycle gas stream. Cooling the entire cycle gas stream produces a two-phase gas-liquid mixture in temperature equilibrium with each other so that the liquid contained in the gas stream does not immediately flash into vapor. Instead, a substantially greater amount of cooling than previously thought possible takes place because the total mass of both gas and liquid enters the polymerization zone at a temperature substantially lower than the polymerization zone. This process led to substantial improvements in the yield of polymers produced in the gas phase, especially where comonomers which can condensate at the temperatures of the polymerization zone, are used. This procedure, commonly referred to as "condensing mode" operation, is described in detail in U.S. Pat. Nos. 4,543,399 and 4,588,790 which are incorporated by reference.

In condensing mode operation, the two-phase gas-liquid mixture entering the polymerization zone is heated quite rapidly and is completely vaporized within very short distance after entry into the polymerization zone. Even in the largest commercial reactors, soon after entry into the polymerization zone all liquid has been vaporized and the temperature of the then totally gaseous cycle gas stream raised, by the exothermic nature of the polymerization reaction. The ability to operate a gas phase reactor in condensing mode was believed possible due to the rapid heating of the two-phase gas liquid stream entering the reactor coupled with efficient constant back mixing of the fluidized bed leaving no liquid present in the polymer bed more than a short distance above the entry level of the two-phase gas-liquid recycle stream.

Commercial polymerization operations have used for years relatively high levels of condensate in the recycle streams, in many instances in excess of 20 weight percent liquid was contained in the recycle stream but always above, the dew point for components in the polymerization zone to assure quick volatilization of the liquid.

While fluidized bed polymerization processes have found particular advantage in the manufacture of polyolefins, the types of polymerization catalysts have been limited to those which are operable in the gas phase. Consequently, catalysts that exhibit activity in solution phase reactions and those which operate by ionic or free radical mechanisms are typically not suitable for in gas phase polymerization processes.

SUMMARY OF THE INVENTION

We have now found that in gas phase polymerization processes, by providing at least one component in the polymerization zone, which component is capable of being liquid under the temperature, pressure and its concentration in the polymerization zone (herein referred to as "Liquid Component"), the polymerization process is enhanced. The concentration of the Liquid Component is maintained in the process of this invention, below that which unduly adversely affects the ability of the polymer bed to be fluidized.

Enhancements that may be achieved in accordance with this invention include one more of the following: increases in production rate; improved catalyst productivity (particularly for catalysts that tend to deactivate, or exhibit accelerated rates of deactivation, with increasing temperature) leading to reduced catalyst residues and lower catalyst costs; reduction in localized regions of higher temperature ("hot spots") in the polymerization bed, facilitated operation control particularly for maintenance of desired temperatures; practical ability to operate at temperature closer to the fusion temperature of the polymer particles being produced since the Liquid Component provides better heat control; improved operation through reduction in the generation of static; improved ability to make sticky polymers; reduction in the risk of fusion of polymer upon emergency shut-down of the reactor; improved ability to operate at higher bed density ratios; improved efficiency in conversion of monomers to polymers through the reduction of fines exiting the polymerization zone and reduced fouling within the reaction system of the type caused by the presence of fines; enhanced ability to control comonomer incorporation in a copolymer; ability to use catalysts that otherwise would not be attractive for fluid bed polymerization processes such as ionic and free radical catalysts; enhancements in the use of solution catalysts for gas phase polymerizations; an ability to enhance the polymer product through morphology control and incorporation of other polymers and additives; an ability to achieve more uniform product properties via more uniform temperatures between different particles and within polymer particles during polymerization, through morphology control, and through incorporation of other polymers and additives.

The processes of this invention involve the production of polymer by the reaction, usually exothermic, of one or more monomers in a fluidized bed reaction vessel having a polymerization zone containing a bed of growing polymer particles. The fluidized bed may be maintained solely by the upwardly flowing gases or may be a stirred bed process. Stirred bed processes are those in which the stirrer cooperates with an upwardly directed flow of gases to assist in the fluidization of the polymer particles. In general, the processes comprise:

a) continuously or intermittently introducing the one or more monomers into said polymerization zone;

b) continuously or intermittently introducing at least one polymerization catalyst into said polymerization zone;

c) continuously or intermittently withdrawing polymer product from said polymerization zone;

d) continuously withdrawing gases from the polymerization zone, compressing and cooling said gases for recycle to the polymerization zone; and e) continuously maintaining sufficient gas flow through the polymerization zone to maintain the bed in a fluidized state, said gas flow comprising recycle of at least a portion of the gases withdrawn from the polymerization zone, wherein at least one Liquid Component is provided in the polymerization zone. A bed is fluidized where substantially all the particles in the bed are suspended in the gas and the particles behave like a fluid.

In one preferred embodiment of the invention, the Liquid Component is provided in the polymerization zone in an amount greater than that which can be absorbed by the polymer particles, and the amount of the Liquid Component that is in excess of the amount that can be absorbed by the polymer particles, is capable of being in the liquid phase throughout the polymerization zone. Preferably, the Liquid Component is provided in an amount of at least 1 percent by weight based upon the weight of the bed.

In another preferred embodiment, the Liquid Component is provided throughout the polymerization zone in liquid and gaseous phases, and is present in the gases in an amount sufficient that substantially no net vaporization of liquid phase Liquid Component into the gaseous medium occurs in the polymerization zone. Thus, the amount of Liquid Component in the liquid phase in the polymerization zone is substantially constant under steady state operating conditions.

In another preferred embodiment, sufficient liquid component is provided to enable the bed to be reduced in height to a level below that which could be obtained by substantially the same process but having the liquid component replaced with an inert, non-condensable gas. The liquid component in the gas and on or in the polymer particles can significantly change the fluidization properties such that this turn-down can be achieved. The turn down enables transitions from one catalyst or polymer to another to be achieved rapidly and with the production of minimal off-grade polymer.

In another preferred embodiment, the Liquid Component permits the polymerization zone to be operated at a high bed density ratio ("FBD") (settled bed density divided by fluidized bed density). In this embodiment, the Liquid Component is provided in the polymerization zone in an amount sufficient to increase the bed density above that achieved by a similar process but in which the liquid component is replaced with an inert, non-condensable gas. Advantageously, the Liquid Component is provided in an amount such that the bed density is increased by an amount of at least about 10, preferably at least about 20, percent of the different between 1.0 and $FBD_s$ wherein $FBD_s$ is the bed density achieved using the inert, non-condensable gas in place of the liquid component.

In another preferred embodiment, the at least one Liquid Component is provided in an amount such that the gases withdrawn from the polymerization zone contain at least a portion of the Liquid Component in the liquid phase.

In another preferred embodiment, the at least one Liquid Component is provided in an amount sufficient to substantially eliminate the generation of static in the polymerization zone.

In another preferred embodiment, the at least one Liquid Component is provided in an amount sufficient to substantially eliminate or reduce the presence of fines in the gases withdrawn from the polymerization zone. Preferably, the fines in the gases withdrawn from the polymerization zone are reduced by at least about 50 weight percent as compared to those in a similar process but having the Liquid Component replaced with inert, non-condensable gas. Often fines having a major dimension of less than about 75 microns, and preferably less than about 100 microns, are substantially eliminated from the gases leaving the polymerization zone as compared to a similar process but not containing the Liquid Component.

Another preferred embodiment of this invention relates to producing polymer particles that are sticky at the temperature of the polymerization zone. In this aspect, the at least one Liquid Component is provided in an amount sufficient to substantially prevent undue agglomeration of polymer particles in the polymerization zone. Undue agglomeration results in the formation of particles that are so large as to disrupt the fluidization of the bed or cause fouling of the reaction vessel walls or are larger than desired for polymer product. Generally, unduly large agglomerates have a major dimension greater than about 5, sometimes greater than about 2, centimeters. In this feature of the invention, the Liquid Component preferably has a limited solubility in the polymer and the Liquid Component is provided in an amount in excess of that which can be dissolved in the polymer in the polymerization zone.

Another preferred embodiment of the invention relates to the production of polymer, wherein upon loss of the gas flow to maintain the bed fluidized and the polymer particles settle in the presence of monomer, the exothermic polymerization reaction can continue and increase the temperature of the polymer particles to a temperature at which the particles stick together or fuse. In this feature, the at least one Liquid Component is provided in an amount sufficient to delay or prevent an increase in the temperature within the settled polymer bed to a temperature at which the unfluidized particles fuse. If the undue temperature rise is delayed, the delay should be for a time sufficient to introduce a kill agent to stop the polymerization, e.g., for at least about 5 minutes, preferably, at least about 10 minutes. Kill agents are well known in the art. Preferably, the Liquid Component is provided in an amount sufficient to prevent localized fused regions greater than about 30 centimeters in major dimension, from forming.

Beyond the reduced risk of polymer fusion one can take further advantage of this feature of the invention by increasing the polymerization zone temperature closer to the particle fusing temperature. In commercial fluid bed operations a healthy temperature margin is often left between the polymerization zone temperature and the polymer fusing temperature to avoid the risk of fusing. Increasing the polymerization zone temperature enables a greater polymer production rate out of existing or new equipment than would be obtained at lower temperatures. This occurs due to the greater heat removal capacity due to a greater temperature difference between the recycle gas stream and the cooling water temperature. Furthermore this enables catalysts to be operated at higher temperatures than were possible before without undue risk of polymer fusion. Some catalysts will have higher productivity or other performance advantages and/or make better products in the newly accessible temperature region.

In another preferred embodiment of the invention, the at least one Liquid Component is provided in an amount sufficient to enhance the production rate of polymer, even at the same average bulk temperature in the polymerization zone. Preferably, the observed increase in production rate is at least about 5 percent as compared to that provided by substantially the same process but replacing the at least one Liquid Component with an inert, non-condensing gas, wherein the dew point of said at least one Liquid Component under the conditions of the polymerization zone is within about 2° C. of the average bulk temperature of the polymerization zone.

Another preferred embodiment of this invention relates to processes deleteriously high localized temperatures can be generated due to the exothermic nature of the polymerization reaction. These temperatures may, for example, tend to deactivate the catalyst or accelerate the polymerization reaction to a level where the heat removal capacities are insufficient to control temperature. In this feature, the at least one Liquid Component is provided in an amount sufficient to protect the catalyst from deleteriously high, localized temperatures. Hot spots can be avoided in that heat generated by the polymerization is absorbed by the mass of Liquid Component present and, if the Liquid Component is capable of being vaporized, is consumed in the vaporization of at least a portion of the Liquid Component in the region. Some or substantially all the Liquid Component that is vaporized may condense in the cooler sections of the polymerization zone or outside the polymerization zone. In a preferred embodiment, where highly active spots exist on the catalyst and localized generation of heat increases, the Liquid Component is vaporized to prevent unduly deleterious high temperatures from being achieved. In some instances, where localized regions of heat are generated that cause growing polymer particles to undergo undue agglomeration, the volume increase associated with the vaporization of Liquid Component may physically break apart the agglomerate and facilitate cooling of the region by the fluidizing gases.

Another preferred embodiment of this invention relates to processes for producing copolymer by the reaction of two or more monomers. The monomers may be continuously or intermittently introduced simultaneously or separately into the polymerization zone. The at least one Liquid Component, where sorbed on and in the growing polymer particles, is capable of affecting the rate of incorporation into the polymer of at least one monomer as compared to at least one other monomer. For instance, the Liquid Component sorbed on the growing particles may be rich in one or more of the monomers as compared to at least one other of the monomers as a means to promote preferential monomer incorporation. By way of example, one or more monomers may have preferential solubility in the Liquid Component and thus affect comonomer concentration at the catalytic site and its relative rate of incorporation into the polymer on a continuous basis. In one embodiment, the Liquid Component may become depleted of this monomer and thus the composition of the polymer particle may change during the time that it is in the polymerization zone, and a given polymer chain may have differing amounts of comonomer incorporation over its length. In a preferred embodiment of this aspect of the invention, ethylene is a monomer and the at least one other monomer has a reactive olefinic bond and from 3 to 36 carbon atoms.

Another preferred embodiment of this invention facilitates or enables the use of polymerization catalysts that are solution, ionic or free-radical catalysts in a gas phase process. In this feature, the at least one Liquid Component is in contact with the catalyst in an amount sufficient for the catalyst to effect the polymerization. Thus, the Liquid Component provides the media to enable the catalyst to function or function more effectively.

BRIEF DESCRIPTION OF THE DRAWING

The drawing is a schematic depiction of an apparatus suitable for carrying out processes in accordance with this invention.

DETAILED DESCRIPTION OF THE INVENTION

A Liquid Component that can be used in accordance with this invention is a material that is capable of being in the liquid phase under the temperature and pressure in the reaction zone taking into account the materials and concentrations in the reaction zone. One way of expressing whether or not a component is capable of being in the liquid phase is by reference to its dew point in the environment. The dew point is the temperature at which a gaseous medium containing a component becomes saturated in the component. Thus, the dew point takes into account temperature, pressure and physical properties of other gases in the gaseous medium. At a temperature at or below the dew point of a component in the gaseous medium, a component in the liquid phase will not evaporate or vaporize into the gaseous medium, but it will vaporize or evaporate if the temperature of the gaseous medium is above the dew point. If the gaseous medium contains greater than a saturation amount of a component, an amount of the component in excess of the saturation amount should condense out or precipitate from the gaseous medium. A gas phase polymerization zone is a dynamic system with localized temperature variations, continuously replenished gases for fluidization, reactions occurring and the like and thus a calculated dew point, which reflects an equilibrium system, may not accurately portray conditions within the polymerization zone. Hence, under steady state conditions in the polymerization zone, liquid can be present throughout the polymerization zone even though the temperature is above the calculated dew point for the liquid in the gaseous medium under the conditions of the polymerization zone. The highest average bulk temperature of the polymerization zone at which, in the presence of Liquid Component in the liquid phase, no net vaporization of liquid into the gaseous medium occurs under steady state operating conditions, is referred to as the practical dew point. Usually, the practical dew point is no more than 2° C., and sometimes no more than 0.5° C., below the calculated dew point. Unless otherwise state, reference to dew point will be to the calculated dew point.

The Liquid Component is provided in the polymerization zone in an amount, or concentration, sufficient that under the conditions in the reaction zone, the practical dew point of the Liquid Component in the fluidizing gases is approximately at the average bulk temperature of the polymerization zone, but not in an amount, or concentration, that adversely affects the fluidization of the bed. Usually, the Liquid Component is provided in an amount, or concentration, such that its calculated dew point in the fluidizing gases under the conditions of the polymerization zone is within about 2° C., preferably within about 0.5° C., of the average bulk temperature of the reaction zone.

While a characteristic of commercial scale fluidized or stirred beds that are fluidized by a gas, is a relative uniformity of temperature throughout the bed due to the circulating currents of fluidized particles and the passage of the large volume of gases through the bed that is necessary for maintaining the fluidized state, localized temperature differentials can and often do exist. For purposes of this invention, the average bulk temperature of the reaction zone is determined by the average of the temperature of the reaction zone at a mid point (the region between 30 to 70 percent of the weight of the bed) and the temperature at or slightly above the top of the bed. In the event that adequate temperature sensors are not provided to ascertain the average bulk temperature, the average bulk temperature can be estimated as the temperature of the gases in the region proximate to the top of the bed.

The pressure in the polymerization zone changes over the bed height. The pressure for purposes of the calculated dew point calculation is the pressure of the gases leaving the top of the polymerization zone.

The amount, or concentration, of the Liquid Component is below that which would adversely affect the fluidization properties in the bed. Adverse effects include promotion of undue agglomeration of fluidized polymer particles (either within the bed or on the walls of the reaction vessel) and undue disengagement of Liquid Component from the fluidized bed such as evidenced by Liquid Component pooling at the bottom of the reaction zone or reaction vessel. Preferably, the Liquid Component is provided in an amount not exceeding that where the gaseous phase would cease to be the continuous phase in the polymerization zone, i.e., a gas phase has a continuous path through the polymerization zone.

The Liquid Component may be present in the polymerization zone both in the vapor phase and liquid phase, and only Liquid Components that have a very low vapor pressure will be, for all practical purposes, essentially entirely in the liquid phase. The liquid phase may be in the form of a free liquid droplet or liquid adsorbed or absorbed on the polymer particle or a combination thereof. Absorbed Liquid Component is that which enters into a chemical reaction or has a chemical interaction or association with the polymer. Absorbed liquid Component may be in equilibrium with Liquid Component in the gas phase, but, all other things being equal, the mole fraction in an inert, non-condensable gas that is in equilibrium with the absorbed Liquid Component will be substantially less than that the mole fraction in equilibrium with the Liquid Component per se. Hence, Absorbed Liquid Component implies more than having a Liquid Component that is miscible with the polymer. Adsorbed Liquid Component is liquid that resides on the polymer by physical attraction or occlusion.

Absorbed Liquid Component does not generally have a material effect on dew point calculations and can often be excluded from calculations determining the dew point based upon total Liquid Component in the polymerization zone. Thus, if the polymer present in the polymerization zone is capable of absorbing 5 kilograms of Liquid Component and at the conditions of the polymerization zone, the gases would be saturated with Liquid Component at a content of 7 kilograms of Liquid Component, then 12 kilograms of Liquid Component must be provided to operate the polymerization zone at its dew point. Any additional Liquid Component above 12 kilograms would essentially be adsorbed or free Liquid Component.

The total amount of liquid on a polymer particle less that amount which can be dissolved in the polymer is the adsorbed liquid. Depending upon the polymer being formed and the processing conditions, significant interstitial void volume may exist within a polymer particle. This void space may increase if the polymer is solvated, for example, with the Liquid Component. Hence, frequently, from about 15 to 25 volume percent of the polymer particle may be void space and available for adsorption of Liquid Component.

In an advantageous embodiment of this invention, the Liquid Component is present in an amount such that its liquid phase is substantially entirely on or in the polymer particles in the bed. In another advantageous embodiment, Liquid Component is present as fine droplets in the polymerization zone, e.g., as a fog. In order to form the fog, the liquid droplets are of a size that enables a relatively stable suspension of the droplets in the upwardly flowing gases, i.e., the droplets have a settling velocity that is relatively low in comparison to the velocity of the gases. Generally, where present, the liquid droplets are less than about 10 microns in diameter. The fog flows substantially with the fluidizing gases and is recirculated to the polymerization zone. Typically, the fog comprises less than about 20, often less than about 10, weight percent Liquid Component in the liquid phase, based on the total weight of the gas phase and entrained liquid. The presence of liquid phase Liquid Component in the gases withdrawn from the polymerization zone can, in some instances, assist in minimizing fouling of piping and equipment for recycling the gases, and advantageously, the Liquid Component is provided in an amount sufficient to such reduce fouling. If desired to minimize potential damage to a compressor for recycling gases to the polymerization zone, the gases may be preheated to reduce the amount of liquid present prior to introducing them into the compressor.

Any Liquid Component that is in the gaseous phase in the gases withdrawn from the polymerization zone may be recycled to the polymerization zone. This vaporous Liquid Component may be condensed during the processing of the recycle stream and, if desired, introduced into the polymerization zone as a liquid. In some instances, a portion of the liquid phase Liquid Component may flash upon being introduced into the polymerization zone and thus serve to cool the polymerization zone.

Often, the liquid phase of the Liquid Component, or the sum of all Liquid Components where more than one is present, is at least about 1, frequently less than about 50, sometimes between about 1 and 40, e.g., between about 2 and 25, weight percent of the fluidized bed. The weight of the fluidized bed can be calculated from the pressure drop of the gases passing through the bed and the cross-sectional area of the bed. The total amount of Liquid Component in the polymerization zone (that which is gaseous and that which is liquid) may vary widely, especially if a substantial portion of the Liquid Component is in the gaseous phase. Generally, the total amount of Liquid Component is at least about 1, frequently less than about 75, sometimes between about 1 and 60, e.g., between about 2 and 30, weight percent based on the weight of the fluidized bed. Often, less than about 75, preferably less than about 50, and in many instances, from virtually none to less than 25, weight percent of the Liquid Component is in the vapor phase in the polymerization zone.

Materials suitable as the Liquid Component will depend upon the desired conditions of the polymerization zone. Thus, with higher temperature and lower pressure operations, materials would be excluded that would otherwise be suitable in higher pressure or lower temperature operations. Another condition affecting the practical dew point is the concentration of the Liquid Component in the reaction zone. For example, Liquid Components requiring unduly high concentrations in the vapor phase to achieve a calculated dew point at or above the conditions in the reaction zone, may be impractical in commercial operations.

The Liquid Component may be reactive or substantially non-reactive in the polymerization reactions; however, the Liquid Component should not unduly adversely affect the polymerization catalysts, the polymerization reaction or the polymer product, especially morphology and other physical properties. Environmental and toxicological issues may also play roles in the selection of the Liquid Component. Illustrative Liquid Components include substantially inert chemical compounds, solvents for one or more monomers or additives to the polymerization zone, monomers, and polymers for physical or chemical incorporation into the polymer product, e.g., substituted and unsubstituted alkanes, alkenes, alkadienes, cycloaliphatics, and aromatics of up to 30 carbons, e.g., propane, propylene, butane, isobutane, butene-1, butene-2, isobutene, 1,2-butadiene, 1,3-butadiene, n-pentane, pentene-1, penten-2, isopentane, n-hexane, 2-methyl pentane, hexene-1, hexene-2, 4-methyl hexene, cyclohexane, cyclohexene, benzene, n-heptane, toluene, n-octane, octane-1, xylene, n-decane, decene-1, dodecane, dodecene-1, cetane, mineral oils, hexadecene-1, octadecane, octadecene-1 and the like. Materials containing heteroatoms may also find application as Liquid Components. The heteroatoms may be one or more of nitrogen, oxygen, silicon, phosphorus, boron, aluminum and sulfur. These Liquid Components have up to about 30 carbon atoms and may be non-cyclic or cyclic and include amines, ethers, thioethers, phosphines, etc. Exemplary materials are triethyl amine, triethylene tetraamine, pyridine, piperazine, tetrahydrofuran, diethylether, di-t-butyl ether, silanes, silicone oils and the like.

Where polyolefins are the polymer product (polyolefins being defined herein as polymers made from monomers having one or more reactive carbon-carbon unsaturated bonds and thus includes olefins, dienes, trienes, etc.), the Liquid Component may contain one or more monomers. Examples of these monomers include the following:

A. alpha olefins such as ethylene, propylene, butene-1, isobutylene, 4-methyl pentene, hexane-1, octene-1, decene-1, dodecene-1, etc. and styrene.

B. dienes such as hexadiene, vinyl cyclohexene, dicyclopentadiene, butadiene, isoprene, ethylidene norbornene and the like, and C. polar vinyl monomers such as acrylonitrile, maleic acid esters, vinyl acetate, acrylate esters, methacrylate esters, vinyl trialkyl silanes and the like.

In an advantageous embodiment of this invention, the polymer product is a polyolefin, preferably ethylene copolymer, propylene copolymer or polybutene or butene copolymer, that is made using an alpha olefin monomer that is procured in combination with non-reactive alkanes and alkenes that are condensable in the polymerization zone. Thus the processes of this invention permit the use of less pure, and thus less expensive, alpha olefin feeds due to the ability to accommodate liquid in the polymerization zone. Often, the feed stream comprises at least about 50, preferably at least about 75, and most frequently at least about 90, up to about 95, weight percent reactive alpha olefin with the balance usually consisting of substantially non-reactive hydrocarbons such as alkanes and alkenes. For instance, where butene-1 is a desired monomer, the butene process streams may contain about 50 to 95 mole percent butene-1, 0 to about 40 mole percent isobutene, 0 to about 40 mole percent butene-2, 0 to about 40 mole percent butane, and 0 to about 40 mole percent isobutane.

In another advantageous aspect, the polymer is polyolefin, particularly ethylene copolymer or propylene copolymer, and at least one comonomer to be incorporated is a high molecular weight alpha-olefin, e.g., from about 12 to 40 carbon atoms. Incorporation of the comonomer provides beneficial properties to the polyolefin including clarity, processability, strength and flexibility. Indeed, polyethylene can be produced with high molecular weight olefin to produce a product in the gas phase process that is comparable in performance to the long chain branched polyethylene obtained by the high pressure process. Sometimes in these processes, the high molecular weight olefin is provided in solution with another Liquid component to provide desirable concentrations of the higher molecular weight olefin on the growing catalyst particle for the sought degree of incorporation. Depending upon the activity of the catalyst for incorporation of the higher olefin, too great a concentration at the catalytic site may effect too much incorporation and too low a concentration may result in little or no incorporation of the higher olefin into the copolymer. Often, the concentration of higher olefin in total Liquid Component is at least about 0.1 or 0.5, say, between about 1 and 75, frequently between 1 and 30, percent by weight based on the weight of the polymer.

In another advantageous aspect of this invention, the Liquid Component comprises a polymer, physical or chemical modifier or additive. Since the modifiers and additives are present during formation of the polymer, intimate and relatively uniform incorporation can occur. Moreover, energy intensive blending and milling operations may be avoided. Further, the relatively uniform dispersion throughout the polymer may enable the amount of the additives to be reduced in comparison to the amounts required during blending operations to achieve the same effects. The modifiers and additives should not unduly adversely affect the polymerization reaction. Generally, the amount of the modifiers and additives provided by the Liquid Component comprises at least about 10, say, at least about 100, parts per million by weight in the polymer product up to about 25, often up to about 15, weight percent of the polymer product. The amount of additives desired to be incorporated into the polymer product is within the skill of those of ordinary skill in the art.

Examples of modifiers and additives that have found application in polymers include antioxidants, stabilizers, processing aids, fluidization aids, antiblock agents, agents to promote blockiness, latent cross linking agents, grafting agents, compatibilizing agents (for instance, to enable the formation of polymer blends), inorganic solids, fillers, dyes, pigments, etc. Examples of modifiers and additives that have found application in polymers include thermo- and photo-oxidation stabilizers such as hindered phenolic antioxidants, dialkylthioester stabilizers, dialkyldisulfide stabilizers, alkyl or aryl phosphite or phosphonite stabilizers, and hindered amine light stabilizers; crosslinking agents such as sulfur and sulfur compounds such as metallic thiocarbamates, dicumyl peroxide, butyl cumyl peroxide and di-t-butyl peroxide; colorants such as carbon black and titanium dioxide; fillers or extenders such as calcium carbonate, kaolin, clay and talc; filler coupling reagents such as silanes and titanates; internal and external lubricants or processing aids such as metallic stearates, hydrocarbon waxes, fatty acid amides, glyceryl stearate esters and silicone oils; oil extenders such as paraffinic and naphthenic mineral oil and silicon oils; grafting reagents such as maleic anhydride and vinyl silanes; chemical blowing reagents such as modified azodicarbonamide, azodicarbonamide and diphenyloxide-4, 4'-disulphohydrazide; compatibilizing compounds such as block polymers of either butadiene or other polymerizable hydrocarbons, styrenic, alkyl acrylate or caprolactone segments for example; flame retardants such as brominated or chlorinated organics, hydrated alumina, magnesium hydroxide and antimony oxide; and other conventional materials that may be mixed with polymer as desired. Advantageously, additives or modifiers that would be expected to be solids under the conditions of the polymerization zone, e.g., di-n-octyl diphenylamine, may find use in the processes of this invention be being dissolved or suspended in Liquid Component.

One attractive class of additives that can be used in accordance with this invention are physical property modifiers, especially for polyolefins. The properties modified include processability, e.g., through extrusion; clarity; and freedom from stress cracks. Illustrative modifiers are mineral oil, dodecylphenol, dodecylbenzene, hexadecane, eicosane, diphenyl(2-ethylhexyl)phosphate, tri(2-ethylhexyl)phosphate, diisoctyl phthalate, di(2-ethylhexyl) phthalate, didecyl phthalate, di-n-octyl phthalate, di-capryl phthalate, turpentine, pine oil, tetralin, di(2-ethylhexyl) adipate, polyethylene glycol di(2-ethylhexoate), didecyl adipate and isooctyl palmate.

Another class of additives that are attractive for use in accordance with the processes of this invention are polymers, including prepolymers, that are carried in Liquid Component, either solvated or as a slurry. The polymers can be for blending with the polymer produces or for reaction with the polymer. In this manner, the properties of the ultimate product can be readily optimized. For instance, a polymer from a separate polymerization zone may have a set of properties that cannot be obtained in the fluid bed polymerization zone of the processes of the invention, and this polymer can become inherently blended with the polymer being grown to produce a polymer blend, or alloy. Advantageously, where the polymers to be blended have limited compatibility, the Liquid Component contains a mutual solvent or compatibilizing agent. Alternatively, the polymer introduced into the polymerization zone has sites reactive under the conditions in the polymerization zone and a block polymeric structure is produced. As can be readily appreciated, the processes of this invention permit the linking of disparate types of polymerization processes with gas phase processes to achieve a balance of product qualities from the introduced polymer and the economic efficiencies of the gas phase process. Generally, where polymer is introduced, the polymer is at least about 1often at least about 2, say, about 2 to 60, weight percent of total polymer product. One particularly attractive process is producing an alloy of polyethylene and polypropylene in a weight ratio of about 10:1 to 1:10, say, about 5:1 to 1:5. In this process, one of the polymers, e.g. polypropylene, is introduced into the polymerization zone with a compatibilizing Liquid Component, e.g., mineral oil, and the polymer product is an alloy. Also, the processes allow the linking of a solution or liquid suspension process and a gas phase polymerization process without the intermediate need to remove substantially all of the liquid carried with the polymer from the solution or liquid suspension process.

Liquid Components can enhance the morphology of the polymer product. Morphology falls within three general classes: surface regularity, internal structure and size. In some instances, lack of surface regularity of products from fluid bed polymerizations results in handling difficulties including reduced flowability and tendency to abrade and generate fines. The presence of Liquid Component often enhances the production of polymer particles with enhances surface morphology as compared to product made by substantially the same process but having an inert, non-condensable gas used in place of the Liquid Component. Often the product of a gas phase polymerization is granular in nature while consumers typically desire pellet form product. To meet consumer desires, granular product has been processed in pelletizers. The presence of the Liquid Component can make each of the granular particles more spherical in shape and can promote agglomeration of a small number of particles to form a pellet-sized polymer product, e.g., from about 0.5 or 1 to about 10 millimeters in major dimension. The amount of Liquid Component required will vary depending upon the polymer, the sought size of the polymer particle and the effectiveness of the Liquid Component as a solvent. If too little or too much Liquid Component is present, undue agglomeration may occur. For instance, many Liquid Components have a solvating or swelling effect on the polymer, and if unduly large amounts of Liquid Component are used the polymer particle may become unduly soft or tacky that large agglomerates or sheeting at the walls of the reaction vessel occur. The solvating effect, however, can be a useful characteristic to enhance the morphology of the polymer product.

POLYMERS AND CATALYSTS

The practice of this invention is not limited to any particular class or kind of polymerization or catalyst. Any catalyst useful in the conduct of gas phase polymerization reactions or that can be used in the presence of Liquid Component is suitable for use in the practice of this invention.

This invention finds particular applicability to the polymerization of olefins, especially olefin polymerization reactions involving homopolymerization and copolymerization. The term copolymerization as used herein includes polymerization with two or more different of monomers. Advantageously, the polymerization includes polymerization with one or more high boiling monomers. Examples of monomers have been set forth above.

Where a copolymer is to be made, the Liquid Component can be selected to affect the relative rates of incorporation of the monomers. For instance, one or more monomers may substantially be in the gaseous state under the conditions of the polymerization while one or more other monomers may be substantially in the liquid state under those conditions. The Liquid Component may essentially consist of the liquid monomers or may also comprise a liquid that is miscible with the liquid monomers. The concentration of the monomers in the Liquid Component sorbed on the growing catalyst particle can influence the rate of incorporation of such monomers into the polymer chain. Often, the lighter monomer in making polyolefin copolymers is ethylene or propylene and the heavier monomer which is at least in part in the liquid phase, is propylene (where ethylene is the comonomer) or higher olefin, e.g., a monomer having at least one reactive olefinic bond and having from 3 to about 36 carbon atoms. Also, the monomer in the liquid phase may comprise a prepolymer that is made outside the polymerization zone. Suitable prepolymers are readily discernible to one skilled in the art. The Liquid Component may also have a greater solubility parameter for one or more monomers than one or more other monomers. For example, toluene or n-hexane may be used as a Liquid Component to preferentially sorb vinyl acetate as compared to ethylene to make an ethylene/vinyl acetate copolymer. Other examples include the use of substantially non-reactive compounds that are otherwise similar in structure to the comonomer such as n-hexane for hexene-1 comonomer, n-octane for octene-1 comonomer, etc.

Catalysts for olefin polymerization include the conventional Ziegler-Natta catalysts, by which is meant those formed by reacting a metal alkyl or hydride with a transition metal compound, are preferred in the practice of this invention. Those formed by reacting an aluminum alkyl with compounds of metals of groups I to III of the periodic table are particularly useful.

Illustrative of the catalysts useful in the practice of this invention are the following:

A. Titanium based catalysts such as those described in U.S. Pat. Nos. 4,376,062 and 4,379,758.

B. Chromium based catalysts such as those described in U.S. Pat. Nos. 3,709,853; 3,709,954 and 4,077,904.

C. Vanadium based catalysts such as vanadium oxychloride, vanadium acetyl acetonate, and those described in U.S. Pat. No. 4,508,842.

D. Metallocene catalysts such as those described in U.S. Pat. Nos. 4,530,914; 4,665,047; 4,752,597; 5,218,071, 5,272,236 and 5,278,272.

E. Cationic forms of metal halides, such as aluminum trihalides.

F. Cobalt catalysts and mixtures thereof such as those described in U.S. Pat. Nos. 4,472,559 and 4,182,814.

G. Nickel catalysts and mixtures thereof such as described in U.S. Pat. Nos. 4,155,880 and 4,102,817.

H. Rare earth metal catalysts and mixtures thereof. Other catalysts that may find application due to the presence of the Liquid Component include:

A. cationic catalysts, particularly for the polymerization of isobutylene, styrene, butyl rubber, isoprene rubber and vinyl ethers, such as boron trifluoride (hydrated), aluminum trifluoride, sulfuric acid, hydrochloric acid (hydrated), and titanium tetrachloride;

B. anionic catalysts, particularly for the polymerization of butyl rubber, isoprene rubber, styrene and butyl rubber copolymer, and acrylonitrile) such as alkyl lithiums, $NaNH_2$, and $LiN(Et)_2$; and C. free radical catalysts, particularly for polymerization of butyl rubber, isoprene rubber, styrene, vinyl halide, styrene butyl rubber copolymer, acrylonitrile-butadiene-styrene terpolymer and vinyl esters, such as azobisisobutyronitrile, benzoyl peroxide, acetyl peroxide, t-butyl peracetic acetate, cumyl peroxide, and t-butyl hydroperoxide.

The conditions for olefin polymerization vary depending upon the monomers, catalysts and equipment availability. The specific conditions are known or readily derivable by those skilled in the art. Generally the temperatures are within the range of −10° C. to 120° C., often about 15° C. to 90° C., and pressures are within the range of 0.1 to 100, say, about 5 to 50, bar.

Due to the presence of the Liquid Component, the processes of this invention may be useful for the preparation of condensation polymers. Polymers prepared by condensation processes include polyamides, polyesters, polyurethanes, polysiloxanes, phenol-formaldehyde polymers, urea-formaldehyde polymers, melamine-formaldehyde polymers, cellulosic polymers and polyacetals. These processes are characterized by the elimination of a lower molecular weight by product such as water or methanol. Since the condensation reactions are generally equilibria reactions, the gas phase operation can assist in the removal of the lighter, and much more volatile, by products. In condensation polymerizations, it is generally preferred to provide a growing polymer particle on which Liquid Component comprising one or more of the monomers, is sorbed. In some instances, porous supports may be used to hold Liquid Component and the porous supports are fluidized. The polymer particle may grow within the porous supports or the reaction may proceed by phase transfer mechanisms in which at least one monomer is within the Liquid Component and at least one monomer in the gas phase with polymer growth occurring at the liquid/gas interface.

In some instances, it may be desired to provide as a portion of the Liquid Component, a material that binds the by-product. For instance, if water is the by-product, the Liquid Component may comprise a dehydrating component or azeotrope-forming agent or organic anhydride compound, e.g., methanol, to dehydrate the reaction medium. The condensation polymerization reactions are frequently conducted at temperatures between about 60° and 250° C. and under pressures of up to about 100 bar. In general, lower pressures are preferred to favor the elimination of the by product. The processes may involve the use of catalysts including alkaline and acidic catalysts. These catalysts and their operating conditions are well known to those skilled in the art. Examples of catalysts are acetic anhydride, sulfonic acid, p-toluenesulfonic acid, sulfuric acid, hydrochloric acid, calcium hydroxide, calcium alkoxides, sodium hydroxide, sodium alkoxide, hydroxides and alkoxides of transition metals, antimony compounds, alkaline salts of zinc, magnesium, aluminum, and the like.

In the processes of this invention, an inert gas can be cycles through the reactor. Suitable inert materials for this purpose include nitrogen and saturated hydrocarbons which remain gaseous at a temperature below the temperature selected to be maintained in the polymerization zone. Desirably, the total of the partial pressures of all components in the cycle gas stream is sufficient to allow enough gas to be present in the cycle gas stream to permit practical, steady state, continuous operation. Suitable for this purpose are inert gases such as nitrogen, argon, neon, krypton and the like. Also useful are saturated hydrocarbons such as ethane, propane, butane and the like as well as halogen substituted alkanes such as freon. Other materials which remain gaseous under the desired conditions, such as carbon dioxide, provided they are essentially inert and do not affect catalyst performance, can also be employed.

Nitrogen, because of its physical properties and relatively low cost is a preferred medium for the manufacture of polymers from higher boiling monomers such as styrene, vinyl acetic acid, acrylonitrile, methylacrylate, methylmethacrylate and the like. Alkanes such as ethane and propane which remain gaseous at relatively low temperatures are also preferred.

In accordance with our invention the Liquid Component can be directly introduced into the polymerization zone or carried into the polymerization zone as with the recycle gas stream or catalyst or cocatalyst (where used) feed. For example, the Liquid Component may be sprayed over the top of the fluidized or stirred bed and thus assist in removal of entrained particles from the gases leaving the bed. If an expanded zone is present in the reaction vessel to assist in removal of particles in the gases leaving the bed, Liquid Component may be contacted with its surfaces to remove any polymer particles that may be adhering thereto. Liquid Component may be sprayed into the bed in one or more locations. Liquid component may also be contacted with and wash the walls of the reaction vessel surrounding the polymerization zone to assist in removing particles. The Liquid Component may also assist in adhering catalyst to the growing polymer particles to enhance further growth of the particles to desired sizes.

A fluidized bed reaction system which is particularly suited to production of polymeric materials in accordance with the present invention is illustrated in the drawing. With reference thereto, the reactor 10 consists of a reaction zone 12 and a velocity reduction zone 14.

In general, the height to diameter ratio of the reaction zone can vary in the range of about 2.7:1 to about 4.6:1. The range, of course, can vary to larger or smaller ratios and depends upon the desired production capacity. The cross-sectional area of the velocity reduction zone 14 is typically within the range of about 2.6 to about 2.8 multiplied by the cross-sectional area of the reaction zone 12.

The reaction zone 12 includes a bed of growing polymer particles, formed polymer particles and a minor amount of the catalyst particles fluidized by the continuous flow of polymerizable and modifying gaseous components in the form of make-up feed and recycle fluid through the reaction zone. To maintain a viable fluidized bed, the superficial gas velocity through the bed must exceed the minimum flow required for fluidization, and preferably is at least 0.1 ft./sec above minimum flow. Ordinarily, the superficial gas velocity does not exceed 5.0 ft./sec and usually no more than 2.5 ft./sec is sufficient.

It is essential that the bed always contain particles to prevent the formation of localized "hot spots" and to entrap and distribute catalyst throughout the reaction zone. On start up, the reactor is usually charged with a base of particulate polymer particles before gas flow is initiated. Such particles may be identical in nature to the polymer to be formed or they may be different. When different, they are withdrawn with the desired formed polymer particles as the first product. Eventually, a fluidized bed of desired polymer particles supplants the start-up bed.

A partially or totally activated precursor composition and/or catalyst used in the fluidized bed is preferably stored for service in a reservoir 16 under a blanket of a gas which is inert to the stored material, such as nitrogen or argon.

Fluidization is achieved by a high rate of fluid recycle to and through the bed, typically on the order to about 50 to about 150 times the rate of feed of make-up fluid. The fluidized bed has the general appearance of a dense mass of individually moving particles as created by the percolation of gas through the bed. The pressure drop through the bed is equal to or slightly greater than the weight of the bed divided by the cross-sectional area. It is thus dependent on the geometry of the reactor.

Make-up fluid can be fed to the bed at point 18. The composition of the make-up stream is determined by a gas analyzer 21. The gas analyzer determines the composition of the recycle stream and the composition of the make-up stream is adjusted accordingly to maintain an essentially steady state gaseous composition within the reaction zone.

The gas analyzer is a conventional gas analyzer which operates in a conventional manner to determine the recycle stream composition to facilitate maintaining the ratios of feed stream components. Such equipment is commercially available from a wide variety of sources. The gas analyzer 21 is typically positioned to receive gas from a sampling point located between the velocity reduction zone 14 and heat exchanger 24.

The Liquid Component can be introduced into the polymerization zone in various ways including direct injection through a nozzle (not shown in the drawing) into the bed or by spraying onto the top of the bed through a nozzle (not shown) positioned above the bed, which may aid in eliminating some carryover of fines by the cycle gas stream. The Liquid Component can be introduced into the polymerization zone simply by suspension in the cycle gas stream entering the bottom of the reactor.

To ensure complete fluidization, the recycle stream and, where desired, part of the make-up stream are returned through recycle line 22 to the reactor at point 26 below the bed. There is preferably a gas distributor plate 28 above the point of return to aid in fluidizing the bed. In passing through the bed, the recycle stream absorbs the heat of reaction generated by the polymerization reaction.

The portion of the fluidizing stream which has not reacted in the bed is removed from the polymerization zone, preferably by passing it into velocity reduction zone 14 above the bed where entrained particles can drop back into the bed.

The recycle stream is compressed in a compressor 30 and then passed through a heat exchange zone where heat is removed before it is returned to the bed. The heat exchange zone is typically a heat exchanger 24 which can be of the horizontal or vertical type. If desired, several heat exchangers can be employed to lower the temperature of the cycle gas stream in stages. It is also possible to locate the compressor downstream from the heat exchanger or at an intermediate point between several heat exchangers. After cooling, the recycle stream is returned to the reactor at its base 26 and to the fluidized bed through gas distributor plate 28. A gas deflector 32 is preferably installed at the inlet to the reactor to prevent contained polymer particles from settling out and agglomerating into a solid mass and to prevent liquid accumulation at the bottom of the reactor as well to facilitate easy transitions between processes which contain liquid in the cycle gas stream and those which do not and vice versa. Illustrative of gas deflectors suitable for this purpose is the apparatus described in U.S. Pat. No. 4,933,149.

The selected temperature of the bed is maintained at an essentially constant temperature under steady state conditions by constantly removing the heat of reaction. Generally, no noticeable temperature gradient appears to exist within the upper portion of the bed. A temperature gradient will exist in the bottom of the bed in a layer of about 6 to 12 inches, between the temperature of the inlet fluid and the temperature of the remainder of the bed.

Good gas distribution plays an important role in the operation of the reactor. The fluidized bed contains growing and formed particulate polymer particles, as well as catalyst particles. As the polymer particles are hot and possibly active, they must be prevented from settling, for if a quiescent mass is allowed to exist, any active catalyst contained therein may continue to react and cause fusion. Diffusing recycle fluid through the bed at a rate sufficient to maintain fluidization throughout the bed is, therefore, important.

Gas distribution plate 28 is a preferred means for achieving good gas distribution and may be a screen, slotted plate, perforated plate, a plate of the bubble-cap type and the like. The elements of the plate may all be stationary, or the plate may be of the mobile type disclosed in U.S. Pat. No. 3,298,792. Whatever its design, it must diffuse the recycle fluid through the particles at the base of the bed to keep the bed in a fluidized condition, and also serve to support a quiescent bed of resin particles when the reactor is not in operation.

The preferred type of gas distributor plate 28 is metal and has holes distributed across its surface. The holes are normally of a diameter of about ½ inch. The holes extend through the plate. Over each hole there is positioned a triangular angle iron identified as 36 which is mounted on plate 28. The angle irons serve to distribute the flow of fluid along the surface of the plate so as to avoid stagnant zones of solids. In addition they prevent the polymer from flowing through the holes when the bed is settled.

Any fluid inert to the catalyst and reactants can also be present in the recycle stream. An activator compound, if utilized, is preferably added to the reaction system downstream from heat exchanger 24, in which case the activator may be fed into the recycle system from dispenser 38 through line 40.

In the practice of this invention operating temperatures can extend over a range of from about −100° C. to about 150° C. with temperatures ranging from about 20° or 40° C. to about 120° C. being preferred.

The fluid-bed reactor can be operated at pressures up to about 1000 psi (3895 kPa) and preferably at a pressure of from about 100 psi (390 kPa) to about 350 psi (2413 kPa), for polyolefin resin production. Operation at higher pressures favors heat transfer as an increase in pressure increases the unit volume heat capacity of the gas.

The partially or totally activated precursor composition and co-catalyst (hereinafter collectively referred to as catalyst) is injected into the bed at a rate equal to its consumption at a point 42 which is above distributor plate 28. Preferably, the catalyst is injected at a point in the bed where good mixing with polymer particles occurs. Injecting the catalyst at a point above the distribution plate provides satisfactory operation of a fluidized bed polymerization reactor. Injection of the catalyst into the area below the distributor plate could cause polymerization to begin there and eventually cause plugging of the distributor plate. Injection directly into the fluidized bed aids in distributing the catalyst uniformly throughout the bed and tends to avoid the formation of localized spots of high catalyst concentration which can cause "hot spots" to form. Injection of the catalyst into the reactor above the bed can result in excessive catalyst carryover into the recycle line where polymerization can occur leading to plugging of the line and heat exchanger.

The catalyst can be injected into the reactor by various techniques. It is preferred, however, to continuously feed the catalyst into the reactor utilizing a catalyst feeder as disclosed; e.g., in U.S. Pat. No. 3,779,712. The catalyst is preferably fed into the reactor at a point 20 to 40 percent of the reactor diameter away from the reactor wall and at a height of about 5 to about 30 percent of the height of the bed.

A gas which is inert to the catalyst, such as nitrogen or argon, is preferably used to carry the catalyst into the bed.

The rate of polymer production in the bed depends on the rate of catalyst injection and the concentration of monomer(s) in the reaction zone. The production rate is conveniently controlled by simply adjusting the rate of catalyst injection.

Since any change in the rate of catalyst injection will change the reaction rate and thus the rate at which heat is generated in the bed, the temperature of the recycle stream entering the reactor is adjusted upwards and downwards to accommodate any change in the rate of heat generation. This ensures the maintenance of an essentially constant temperature in the bed. Complete instrumentation of both the fluidized bed and the recycle stream cooling system is, of course, useful to detect any temperature change in the bed so as to enable either the operator or a conventional automatic control system to make a suitable adjustment in the temperature of the recycle stream.

Under a given set of operating conditions, the fluidized bed is maintained at essentially a constant height by withdrawing a portion of the bed as product at the rate of formation of the particulate polymer product. Since the rate of heat generation is directly related to the rate of product formation, a measurement of the temperature rise of the fluid across the reactor (the difference between inlet fluid temperature and exit fluid temperature) is indicative of the rate of particular polymer formation at a constant fluid velocity if no or negligible vaporizable liquid is present in the inlet fluid.

On discharge of particulate polymer product from reactor 10, it is desirable and preferable to separate fluid from the product and to return the fluid to the recycle line 22. There are numerous ways known to the art to accomplish this. One preferred system is shown in the drawings. Thus, fluid and product leave reactor 10 at point 44 and enter product discharge tank 46 through valve 48, which may be a ball valve which is designed to have minimum restriction to flow when opened. Positioned above and below product discharge tank 46 are conventional valves 50, 52 with the latter being adapted to provide passage of product into product surge tank 54. Product surge tank 54 has venting means illustrated by line 56 and gas entry means illustrated by line 58. Also positioned at the base of product surge tank 54, is a discharge valve 60 which when in the open position discharges product for conveying to storage. Valve 50 when in the open position releases fluid to surge tank 62. Fluid from surge tank 62 is directed through a filter absorber 64 and thence through a compressor 66 and into recycle line 22 through line 68.

In a typical mode of operation, valve 48 is open and valves 50, 52 are in a closed position. Product and fluid enter product discharge tank 46. Valve 48 closes and the product is allowed to settle in product discharge tank 46. Valve 50 is then opened permitting fluid to flow from product discharge tank 46 to surge tank 62 from which it is continually compressed back into recycle line 22. Valve 50 is then closed and valve 52 is opened and any product in product discharge tank 46 flows into product surge tank 54. Valve 52 is then closed. The product is purged with inert gas, preferably nitrogen, which enters product surge tank 54 through line 58 and is vented through line 56. Product is then discharged from product surge tank 54 through valve 60 and conveyed through line 20 to storage.

The particular timing sequence of the valves is accomplished by the sue of conventional programmable controllers which are well known in the art. Moreover, the valves can be kept substantially free of agglomerated particles by directing a stream of gas periodically through the valves and back to the reactor.

Another preferred product discharge system which may be alternatively employed is that disclosed and claimed in U.S. Pat. No. 4,621,952. Such a system employs at least one (parallel) paid of tanks comprising a settling tank and a transfer tank arranged in series and having the separated gas phase returned from the top of the settling tank to a point in the reactor near the top of the fluidized bed. Such alternative preferred product discharge system obviates the need a recompression line 64,66,68, as shown in the system of the drawing.

The fluidized-bed reactor is equipped with an adequate venting system (not shown) to allow venting the bed during start up and shut down. The reactor does not require the use of stirring and/or wall scraping. The recycle line 22 and the elements therein (compressor 30, heat exchanger 24) should be smooth surfaced and devoid of unnecessary obstructions so as not to impede the flow of recycle fluid or entrained particles.

Conventional techniques for the prevention of fouling of the reactor and polymer agglomeration can be used in the practice of our invention. Illustrative of these techniques are the introduction of finely divided particulate matter to prevent agglomeration, as described in U.S. Pat. Nos. 4,994,534 and 5,200,477; the addition of negative charge generating chemicals to balance positive voltages or the addition of positive charge generating chemicals to neutralize negative voltage potentials as described in U.S. Pat. No. 4,803,251. Antistat substances may also be added, either continuously or intermittently to prevent or neutralize static charge generation. Condensing mode operation such as disclosed in U.S. Pat. Nos. 4,543,399 and 4,588,790 can also be used to ensure operability of the fluid bed polymerization and to assist in heat removal.

EXAMPLES

The following examples are provided to illustrate our invention.

EXAMPLE 1

In an example of the process of the invention a fluidized bed reaction system as described above, is operated as described below to produce ethylene-propylene diene terpolymer. The polymer is produced under the following reaction conditions: 40° C. reactor temperature and 290 psia reactor pressure. The partial pressures (dew points) of the monomers and comonomers inside the reactor are 90 psia for ethylene and 198 psia for propylene. The partial pressure of hydrogen is 2.0 psia. The monomer ethylidene-norbornene (ENB) is injected into the polymerization zone of the reactor at the rate of 0.53 lb/h. The volume of the reactor is 55 ft$^3$; the resin's weight inside the reactor was 112 lbs. The catalyst system employed in this Example is vanadium acetyl acetonate with diethylaluminum chloride as co-catalyst and ethyl trichloroacetate as the promoter. The production rate is 20 lb/h. The product has a Mooney value of 55.

About 75 percent of the injected ENB is incorporated into the polymers by polymerization. The unreacted remainder of ENB, dissolved into polymers and is equal to 0.66 percent of the polymer's weight. With 112 lbs. of resins inside the reactor, the total unreacted ENB is 0.74 lbs. If the unreacted ENB were completely evaporated inside the reactor, its partial pressure would be 0.6764 psia.

At 40° C. the saturation pressure is 2187.7 psia for ethylene, 337.1 psia for propylene and 0.262 psia for ENB. Since the partial pressures of ethylene and propylene inside the reactor are much less than their saturation pressures, there is no condensed ethylene or propylene. The calculated partial pressure of unreacted ENB inside the reactor, however, is much higher than its saturation pressure. Therefore, the ENB must be in a liquid state and been absorbed by the polymers.

EXAMPLE 2

Ethylene-propylene diene terpolymer is made in a fluidized bed reaction system as described above under the following reaction conditions: 40° C. reactor temperature and 363.4 psia reactor pressure. The partial pressures of the monomers and comonomers inside the reactor are 90 psia for ethylene and 198.2 psia for propylene. The partial pressure of hydrogen is 2.2 psia, and the partial pressure of nitrogen was 72.6. The monomer ethylidene norbornene (ENB) is injected into the polymerization zone of the reactor at the rate of 0.53 lb/h. The volume of the reactor is 55 ft³; the resin's weight inside the reactor was 112 lbs. The catalyst system employed in this Example is vanadium acetyl acetonate with diethylaluminum chloride as co-catalyst and ethyl trichloroacetate as the promoter. The production rate is 20 lb/h. The product has a Mooney value of 55.

Seventy-five percent of the injected ENB is incorporated into polymers by polymerization. The unreacted remainder of ENB, dissolved into polymers and is equal to 0.66 percent of the polymer's weight. With 112 lbs. of resins inside the reactor, the total unreacted ENB is 0.74 lbs. If the unreacted ENB completely evaporates inside the reactor, its partial pressure would be 0.6764 psia.

At 40° C. the saturation pressure is 2187.7 psia for ethylene, 337.1 psia for propylene, and 0.262 psia, for ENB. Since the partial pressures of ethylene and propylene inside the reactor are much less than their saturation pressures, there is no condensed ethylene or propylene. The calculated partial pressure of unreacted ENB inside the reactor, however, is much higher than its saturation pressure. Therefore, the ENB must be in a liquid state and be absorbed by the polymers.

EXAMPLES 3 to 6

Examples 3 to 6 set forth in tabular form, operating conditions for producing a variety of different polymers in accordance with the invention. They illustrate the practice of the invention using different catalyst systems and differing cycle gas compositions.

| EXAMPLE NO. | 3 | 4 | 5 | 6 |
|---|---|---|---|---|
| PRODUCT: | POLYBUTADIENE | SBR | ABS | POLYSTYRENE |
| Reaction Conditions: | | | | |
| Temperature (°C.) | 40 | 40 | 40 | 40 |
| Pressure (psi) | 100 | 110 | 200 | 100 |
| Superficial Velocity (ft/s) | 1.75 | 2.0 | 1.5 | 1.5 |
| Production Rate (lb/h) | 30 | 25 | 20 | 40 |
| Total Reactor Volume (ft³) | 55 | 55 | 55 | 55 |
| Reaction Zone Volume (ft³) | 7.5 | 7.5 | 7.5 | 7.5 |
| Bed Height (ft) | 7.0 | 7.0 | 7.0 | 7.0 |
| Bed Diameter (ft) | 1.17 | 1.17 | 1.17 | 1.17 |
| Bed Weight (lbs) | 112 | 112 | 112 | 112 |
| Cycle Gas Composition: | | | | |
| $N_2$ | 20 | 27.3 | 58.0 | 99.7 |
| Butadiene | 80 | 72.5 | 39.9 | — |
| Styrene | — | .2 | 0.15 | 0.3 |
| Acrylonitrile | — | — | 1.95 | — |
| Catalyst: | Co(acac)₃* | Co(acac)₃* | Co(acac)₃* | $C_{p2}ZrMe_2$** |
| Co-catalyst: | Triethyl-aluminum | Triethyl-aluminum | Triethyl-aluminum | MAO*** |
| Heavy Monomer Feed Rate (lb/h) | | | | |
| Butadiene | 46.2 | 9.62 | 2.46 | — |
| Styrene | — | 20.83 | 15.33 | 44.4 |
| Acrylonitrile | — | — | 7.08 | — |
| Polymer Composition: | | | | |
| Butadiene | 100 | 25 | 8 | — |
| Styrene | | 75 | 69 | 100 |
| Acrylonitrile | | — | 23 | — |

*Cobalt triacetylacetonate
**Dicyclopentadienylzirconiumdimethyl
***Methylalumoxane

EXAMPLES 7 to 10

EXAMPLE 7

A fluidized bed reaction system as described above, is operated as described below to produce polybutadiene. The polymer is produced under the following reaction conditions: 55° C. reactor temperature and 100 psia total reactor pressure. The partial pressure of the butadiene monomer inside the reactor is 80 psia. The partial pressure of nitrogen is 20 psia. The catalyst system employed in this Example is cobalt tris)acetylacetonate). It may be supported on silica or fed as a solution in methylene chloride. methylaluminoxane is used as co-catalyst. Catalyst and co-catalyst feeds are adjusted to give a 400:1 molar ratio of Al to Co. At steady state the monomer is fed into the reaction system at the rate of 47.8 lb/h. Dried N-650 carbon black is fed to the reactor at the rate of 20 lb/h. Butadiene monomer leaves the reactor at 15 lb/h in vent streams. The production rate is 30 lb/h of polymer after adjusting for the carbon black content. The product has a Mooney viscosity ML (1+4@100° C.) of 55. Other conditions are shown for Example 7 in the table.

At steady state a total of 47.8 lb/h butadiene is being fed to the reactor and a total of 45 lb/h is accounted for leaving the reactor as gas in a vent stream or as polymer. The difference of 2.8 lb/h must be unreacted liquid butadiene monomer in the polymer leaving the reactor. Since the polymer discharged is identical with the polymer in the bed, the polymer in the bed must contain the same proportion of liquid monomer, i.e. there must be 10.4 lbs of dissolved liquid monomer in the 112 lbs polymer bed.

The reactor volume is 55 ft$^3$. At the partial pressure of 80 psia, there are 37.6 lbs of butadiene in the reactor gas-phase. The total unpolymerized butadiene in the reactor is thus 48.0 lbs (=37.6+10.4). If all of this butadiene were in the gas phase of this reactor at once it would have a partial pressure of 104 psia and its condensation temperature would be 61° C. Therefore the reactor at 55° C. is being operated below the condensation temperature of the monomer present in the polymerization zone. Furthermore, the presence of this liquid monomer in the gas-phase reactor does not cause agglomeration of the polymer.

| | EXAMPLE NO. | | | |
|---|---|---|---|---|
| | 7 | 8 | 9 | 10 |
| | PRODUCT: | | | |
| | POLYBU-TADIENE | SBR | ABS | POLYISO-PRENE |
| Reaction Conditions: | | | | |
| Temperature (° C.) | 55 | 55 | 55 | 65 |
| Total Pressure (psia) | 100 | 110 | 200 | 100 |
| Superficial Velocity (ft/s) | 1.75 | 2.0 | 1.5 | 1.75 |
| Production Rate (lb/h) | 30 | 25 | 20 | 30 |
| Total Reactor Volume (ft$^3$) | 55 | 55 | 55 | 55 |
| Reaction Zone Volume (ft$^3$) | 7.5 | 7.5 | 7.5 | 7.5 |
| Bed Height (ft) | 7.0 | 7.0 | 7.0 | 7.0 |
| Bed Diameter (ft) | 1.17 | 1.17 | 1.17 | 1.17 |
| Bed Weight (lbs) | 112 | 112 | 112 | 112 |
| Cycle Gas Composition (mole %): | | | | |
| N$_2$ | 20 | 27.3 | 58.0 | 70 |
| Butadiene | 80 | 72.5 | 39.9 | — |
| Styrene | — | 0.2 | 0.15 | — |
| Acrylonitrile | — | — | 1.95 | — |
| Isoprene | — | — | — | 30 |
| Catalyst: | Co(acac)$_3$* | CpTiCl$_3$ | CpTiCl$_3$ | TiCl$_4$ |
| Co-catalyst: | MAO*** | MAO*** | MAO*** | TEAL** |
| Monomer Feed Rate (lb/h) | | | | |
| Butadiene | 47.8 | 9.62 | 2.46 | — |
| Styrene | — | 20.83 | 15.33 | — |
| Acrylonitrile | — | — | 7.08 | — |
| Isoprene | — | — | — | 35.4 |
| Total Monomer Vent Rate (lb/h) | 15 | 1 | 1 | 2 |

-continued

| | EXAMPLE NO. | | | |
|---|---|---|---|---|
| | 7 | 8 | 9 | 10 |
| | PRODUCT: | | | |
| | POLYBU-TADIENE | SBR | ABS | POLYISO-PRENE |
| Polymer Composition (wt. %): | | | | |
| Butadiene | 100 | 25 | 8 | — |
| Styrene | — | 75 | 69 | — |
| Acrylonitrile | — | — | 23 | — |
| Isoprene | — | — | — | 100 |

*Cobalt triacetylacetonate
**also Diphenyl Ether
***Methylalumoxane

EXAMPLES 11 to 21

EXAMPLE 11

To a gas-phase stirred bed reactor that is maintained at a constant temperature of 22° C. 4.2 pounds of dried carbon black powder are added to act as a fluidization aid. To this are added 0.039 lbs ethyl aluminum sesquichloride (EASC). Then is added 0.61 lb of 1,3-butadiene and sufficient nitrogen to bring the total reactor pressure to 315 psia. A small feed of supported CoCl$_2$(pyridine)$_4$ catalyst is begun. Simultaneously, a small feed of 10 wt. % ethyl aluminum sesquichloride co-catalyst solution in isopentane is begun. Feeds are adjusted to give a 15:1 molar ratio of Al:Co. During a 2.2 hour polymerization reaction, a total of 6.84 lbs of additional butadiene is fed in order to replace butadiene that is polymerized or vented. A small vent stream leaving the reactor removes a total of 0.22 lbs butadiene during the polymerization. At the end of the polymerization, the catalyst and co-catalyst feeds are stopped. The reactor is depressurized, and the reactor contents purged free of residual butadiene using nitrogen. The polymer is discharged from the reactor. The product does not contain any lumps that would indicate agglomeration had occurred. To the contrary, the product is a free-flowing, fine, granular powder. The reactor is opened and cleaned to ensure that all product is recovered. The total weight of solid product that is recovered is adjusted for the carbon black that has been initially charged. The remainder (5.73 lbs) is the amount of butadiene polymer formed during the batch and which is present in the reactor when it is shut down. Since a total of 7.45 lbs (=6.84+0.61) of butadiene were charged to the reactor and a total of 5.95 lbs (=5.73+0.22) of butadiene have been accounted for leaving the reactor as polymer and in the continuous vent stream, there must be 1.50 lbs of butadiene monomer present in the reactor when polymerization is terminated. This monomer would be removed from the reactor when it is depressurized and the contents purged.

The reactor volume is 61.7 liters (or 2.18 cubic feet). At 22° C. the vapor pressure of 1,3-butadiene is 35 psia. The mass of butadiene present in the reactor as a gas at saturation would thus be 0.73 lbs. Of the total of 1.50 lbs of unpolymerized butadiene that is shown to be present in the reactor at shutdown, at most 0.73 lbs could be in the vapor phase and the rest (0.77 lbs) must be present in a condensed phase, for example, dissolved in the polymer. Thus the reactor is being operated at a temperature below the condensation temperature of the monomer present. The 0.77 lbs of liquid monomer combined with the 5.73 lbs of polymer amounts to 13.4 lbs of condensed butadiene monomer per 100 lbs of polybutadiene. Yet, the presence of this liquid monomer in the gas-phase reactor does not cause agglomeration of the polymer. The table provides a further summary of the example.

Examples 12 to 21 are conducted as in Example 11, but with the changes indicated in the table. Several particular changes are noted in further detail below.

Supported Catalyst Preparation for Example 12

To a 500 mL dry nitrogen purged flask is added 31.9 grams of silica (600° C. activation) and 7.272 grams of $CoCl_2$ (pyridine)$_4$. To this is added 150 mL of $Ch_2Cl_2$. The slurry is stirred for a few minutes and then the solvent was removed under vacuum.

Solution Catalyst Preparation for Example 18

Into a dry nitrogen purged flask is charged 1.648 grams of cobalt tris acetylacetonate. To this is added 100 mL of dry $Ch_2Cl_2$. The mixture is stirred for a few minutes and charged to a pressurizable metal cylinder and fed to the reactor as a solution.

EXAMPLE 14

To a gas-phase stirred bed reactor that is maintained at a constant temperature of 20° C., 4.2 pounds of dried carbon black powder are added to act as a fluidization aid. To this is added 0.045 lb methyl aluminoxane (MAO). Then are added 1.01 lb of 1,3-butadiene and sufficient nitrogen to bring the total reactor pressure to 315 psia. A small feed of supported $CoCl_2$(pyridine)$_4$ catalyst is begun. Simultaneously, a small feed of 10 wt. % MAO co-catalyst solution in toluene is begun. Feeds are adjusted to give a 607:1 molar ratio of Al:Co. During a 1.33 hour polymerization reaction, a total of 6.50 lbs of additional butadiene are fed in order to replace butadiene that is polymerized or vented. A total of 1.02 lbs of toluene are fed in the initial and continuous feeds of MAO solution. A small vent stream leaving the reactor removes a total of 0.21 lbs butadiene and 0.005 lbs toluene during the polymerization. At the end of the polymerization, the catalyst and co-catalyst feeds are stopped. The reactor is depressurized, and the reactor contents purged free of residual butadiene and toluene using nitrogen. The polymer is discharged form the reactor. The product does not contain any lumps that would indicate agglomeration has occured. To the contrary, the product is a free-flowing, fine, granular powder. The reactor is opened and cleaned to ensure that all product is recovered. The total weight of solid product that is recovered is adjusted for the carbon black that has been initially charged. The remainder (5.81 lbs) is the amount of butadiene polymer formed during the batch and which is present in the reactor when it is shut down. Since a total of 7.51 lbs (=6.50+1.01) of butadiene are charged to the reactor and a total of 6.02 lbs (=5.81+0.21) of butadiene are accounted for leaving the reactor as polymer and in the continuous vent stream, there must be 1.49 lbs of butadiene monomer present in the reactor when polymerization is terminated. This monomer would be removed form the reactor when it is depressurized and the contents purged.

The reactor volume is 6.17 liters (or 2.18 cubic feet). At 20° C. the vapor pressure of 1,3-butadiene is 35 psia. The mass of butadiene present in the reactor as a gas at saturation would thus be 0.73 lbs. Of the total of 1.49 lbs of unpolymerized butadiene that is shown to be present in the reactor at shutdown, at most 0.73 lbs could be in the vapor phase and the rest (0.76 lbs) must be present in a condensed phase, for example, dissolved in the polymer. Thus the reactor is being operated at a temperature below the condensation temperature of the monomer present. The 0.76 lbs of liquid monomer combined with the 5.81 lbs of polymer amounts to 13.1 lbs of condensed butadiene monomer per 100 lbs of polybutadiene.

Similarly, since a total of 1.02 lbs of toluene are charged to the reactor and a total of 0.005 lbs of toluene are accounted for leaving the reactor in the continuous vent stream, there must be 1.015 lbs of toluene present in the reactor when polymerization is terminated. This toluene would be removed from the reactor when it is depressurized and the contents purged. At 20° C. the vapor pressure of toluene is 0.46 psia. The mass of toluene present in the reactor as a gas at saturation would thus be 0.016 lbs. Of the total of 1.015 lbs of toluene that is present in the reactor at shutdown, at most 0.016 lbs could be in the vapor phase and the rest (1.0 lbs) must be present in a condensed phase, for example, dissolved in the polymer. Thus the reactor is operated at a temperature below the condensation temperature of the toluene present. The 1.0 lbs of liquid toluene combined with the 5.81 lbs of polymer amounts to 17.2 lbs of condensed butadiene monomer per 100 lbs of polybutadiene.

Thus, in this example there are a total of 30.3 lbs of condensed butadiene and toluene per 100 lbs of polybutadiene in the gas-phase reactor, yet the presence of these liquid components does not cause agglomeration of the polymer. The table gives further details on this example.

| | EXAMPLE NO. | | | |
|---|---|---|---|---|
| | 11 | 12 | 13 | 14 |
| | PRODUCT: | | | |
| | POLYBU-TADIENE | POLYBU-TADIENE | POLYBU-TADIENE | POLYBU-TADIENE |
| CATALYST DETAILS | | | | |
| Catalyst | Cobalt dichloride-pyridine on silica | Cobalt dichloride-pyridine on silica | Cobalt acetyl acetonate on silica | Cobalt dichloride-pyridine on silica |
| Co-catalyst | 10% EASC in isopentane | 15% DEACO in toluene | 10% EASC in isopentane | 10% MAO in toluene |
| PROCESS CONDITIONS | | | | |
| Reaction Temp. (° C.) | 22 | 23 | 20 | 20 |
| BD partial pressure (psia) | 30 | 30 | 30 | 30 |
| Polymer produced (lb) | 5.7 | 6.3 | 5.4 | 5.8 |
| Reaction time | 2 hr 10 min | 3 hr | 2 hr 15 min | 1 hr 20 min |
| PRODUCT ANALYSIS | | | | |
| % Carbon Black N-650 analysis | 44 | 38 | 44 | 45 |
| Average particle size by sieve analysis (inch) | 0.016 | 0.019 | 0.015 | 0.034 |
| Aluminum/ Catalyst feed ratio* | 15 | 28 | 11 | 607 |

-continued

| | EXAMPLE NO. | | | |
|---|---|---|---|---|
| | 11 | 12 | 13 | 14 |
| | PRODUCT: | | | |
| | POLYBU-TADIENE | POLYBU-TADIENE | POLYBU-TADIENE | POLYBU-TADIENE |
| Cobalt content in the polymer (ppm) | 55 | 81 | 94 | 19 |
| Reduced Viscosity (dl/g) | 1.5 | 1.0 | 1.0 | 3.6 |
| Mooney viscosity ML (1 + 4 @ 100° C.) | | 42 | | |
| % cis-1,4 | 93 | 92 | 92 | 98.4 |

*molar ratio of Al to transition metal in continuous feeds

| | EXAMPLE NO. | | | |
|---|---|---|---|---|
| | 15 | 16 | 17 | 18 |
| | PRODUCT: | | | |
| | POLYBU-TADIENE | POLYBU-TADIENE | POLYBU-TADIENE | POLYBU-TADIENE |
| CATALYST DETAILS | | | | |
| Catalyst | Cobalt dichloride pyridine on silica | Cobalt dichloride pyridine-IPPD† diamine on silica | Cobalt octoate on silica | Cobalt acetyl acetonate in methylene chloride |
| Co-catalyst | 10% MAO in toluene | 15% EASC in toluene | 15% DEACO in toluene | 10% DEAC in isopentane |
| PROCESS CONDITIONS | | | | |
| Reaction Temp. (° C.) | 20 | 20 | 20 | 20 |
| BD partial pressure (psia) | 30 | 30 | 30 | 25 |
| Polymer produced (lb) | 4.2 | 6.5 | 6.8 | 5.7 |
| Reaction time | 1 hr | 4 hr 30 min | 3 hr 10 min | 4 hr 30 min |
| PRODUCT ANALYSIS | | | | |
| % Carbon Black N-650 analysis | 56 | 44 | 41 | 44 |
| Average particle size by sieve analysis (inch) | 0.036 | 0.016 | 0.013 | Size not measured |
| Al/Catalyst feed ratio* | 385 | 62 | 10 | 45 |
| Cobalt content in the polymer (ppm) | 45 | 84 | 195 | 45 |
| Reduced Viscosity (dl/g) | 1.0 | 1.1 | 1.0 | 0.7 |
| Mooney viscosity ML (1 + 4 @ 100° C.) | 40 | | | |
| % cis-1,4 | 95.7 | 96 | 92.1 | 90 |

†N-isopropyl-N'-phenyl-p-phenylenediamine was present on the catalyst at 15 moles per mole of cobalt.
*molar ratio of Al to transition metal in continuous feeds

| | EXAMPLE NO. | | |
|---|---|---|---|
| | 19 | 20 | 21 |
| | PRODUCT: | | |
| | POLYBU-TADIENE | POLYBU-TADIENE | POLYISO-PRENE |
| CATALYST DETAILS | | | |
| Catalyst | Cyclopentadiene titanium trichloride | Nickel octoate | TiCl₄/diphenyl-ether |
| Co-catalyst | 10% MAO in toluene | 10% TEAL 10% BF₃ etherate | TIBA |
| PROCESS CONDITIONS | | | |
| Reaction Temperature (° C.) | 50 | 50 | 50 |
| Monomer partial pressure (psia) | 60 | 60 | 25 |
| Reaction time | 2 hr | 4 hr | 4 hr |
| PRODUCT ANALYSIS | | | |
| % Carbon Black N-650 by analysis | 40 | 40 | 40 |
| Co-catalyst/Catalyst feed ratio* | 500 | 60 | 10 |

*molar ratio of Al to transition metal in continuous feeds

EXAMPLES 22 to 29

EXAMPLE 22

To a gas-phase stirred bed reactor that is maintained at a constant temperature of 60° C., 3.8 pounds of dried carbon black powder are added to act as a fluidization aid. To this is added 0.055 lb TIBA, i.e. triisobutylaluminum. Then are added 1.86 lbs of 1,3-butadiene and sufficient nitrogen to bring the total reactor pressure to 315 psia. A small feed of supported catalyst consisting of neodymium neodecanoate on DEAC-treated silica is begun. Simultaneously, a small feed of 10 wt. % triisobutylaluminum co-catalyst solution in isopentane is begun. Feed is adjusted to give a 7:1 molar ratio of Al:Nd. During a 2.8 hour polymerization reaction, a total of 6.93 lbs of additional butadiene are fed in order to replace butadiene that is polymerized or vented. A small vent stream leaving the reactor removes a total of 0.95 lbs butadiene during the polymerization. At the end of the polymerization, the catalyst and co-catalyst feeds are stopped. The reactor is depressurized, and the reactor contents purged free of residual butadiene using nitrogen. The polymer is discharged from the reactor. The product does not contain any lumps that would indicate agglomeration has occurred. To the contrary, the product is a free-flowing, fine, granular powder. The reactor is opened and cleaned to ensure that all product is recovered. The total weight of solid product that is recovered is adjusted for the carbon black that has been initially charged. The remainder (5.35 lbs) is the amount of butadiene polymer formed during the batch and which is present in the reactor when it is shut down. Since a total of 8.79 lbs (=6.93+1.86) of butadiene are charged to the reactor and a total of 6.30 lbs (=5.35+0.95) of butadiene are accounted for leaving the reactor as polymer and in the continuous vent stream, there must be 2.49 lbs of butadiene monomer present in the reactor when polymerization is terminated. This monomer would be removed from the reactor when it is depressurized and the contents purged.

The reactor volume is 61.7 liters (or 2.18 cubic feet). At 60° C. the vapor pressure of 1,3-butadiene is 103 psia. The mass of butadiene present in the reactor as a gas at saturation would thus be 1.88 lbs. Of the total of 2.49 lbs of unpolymerized butadiene that is present in the reactor at shutdown, at most 1.88 lbs could be in the vapor phase and the rest (0.61 lbs) must be present in a condensed phase, for example, dissolved in the polymer. Thus the reactor is operated at a temperature below the condensation temperature of the monomer present. The 0.61 lb of liquid monomer combined with the 5.35 lbs of polymer amounts to 11.4 lbs of condensed butadiene monomer per 100 lbs of polybutadiene. Yet, the presence of this liquid monomer in the gas-phase reactor does not cause agglomeration of the polymer.

Examples 23 to 29 are conducted as in Example 22, but with the changes indicated in the tables.

Solution Catalyst Preparation for Example 23

Into a dry nitrogen purged flask is charged 12.32 grams of a hexane solution of neodymium neodecanoate (5.4 wt. % Nd in hexane). To this are added 85 mL dry hexane. To this solution are added 3.0 mL of 1.5 M $Et_2AlCl$ (1.0 eq Al/Nd). The mixture is stirred, charged to a pressurizable metal cylinder and fed to the reactor as a solution.

Supported Catalyst Preparation for Example 24

To a 500 mL dry nitrogen purged flask are added 78.15 grams of silica (600° C. activation) and 250 mL dry hexane. Slowly, 40 mL of 1.5M $Et_2AlCl$ are added and the mixture is stirred for 60 minutes at room temperature. The solution is cooled and 117 grams of a hexane solution of neodymium versatate (4.9 wt. % Nd) are added slowly. The mixture is stirred for 30 minutes and then the solvent is removed under vacuum.

| | EXAMPLE NO. | | | |
|---|---|---|---|---|
| | 23 | 24 | 25 | 26 |
| | PRODUCT: | | | |
| | POLYBU-TADIENE | POLYBU-TADIENE | POLYBU-TADIENE | POLYBU-TADIENE |
| CATALYST DETAILS | | | | |
| Catalyst | Neodymium neodecanoate in hexane | Neodymium versatate on DEAC-treated silica | Neodymium versatate on DEAC-treated silica | Neodymium neodecanoate on DEAC-treated silica |
| Cocatalyst | 10% TIBA in isopentane | 10% TIBA in isopentane | 1:3 DIBAH: TIBA in isopentane | 10% DIBAH in isopentane |
| PROCESS CONDITIONS | | | | |
| Reaction Temperature (° C.) | 50 | 60 | 60 | 60 |
| Monomer partial pressure (psia) | 63 | 63 | 63 | 63 |
| Polymer produced (lb) | 6.8 | 5.8 | 6.4 | 4.5 |
| Reaction time | 5 hr | 2 hr 30 min | 2 hr 15 min | 3 hr |
| PRODUCT ANALYSIS | | | | |
| % Carbon Black N-650 by analysis | 42 | 41 | 41 | 42 |
| Average particle size by sieve analysis (inch) | 0.076 | 0.017 | 0.018 | 0.013 |
| Cocatalyst/Catalyst Feed ratio* | 21 | 7 | 9.5 | 11 |
| Neodymium content in the polymer (ppm) | 132 | 288 | 179 | 415 |
| Reduced Viscosity (dl/g) | 12.8 | 10.3 | 7.6 | 4.9 |
| Mooney viscosity (est. gum) ML (1 + 4 @ 100° C.) | | | | 90 |
| % cis-1,4 | 99.1 | 97 | 96.2 | 97 |

| | EXAMPLE NO. | | |
|---|---|---|---|
| | 27 | 28 | 29 |
| | PRODUCT: | | |
| | POLYBU-TADIENE | POLYBU-TADIENE | POLYISO-PRENE |
| CATALYST DETAILS | | | |
| Catalyst | Neodymium neodecanoate on DEAC-treated silica | Neodymium neodecanoate on DEAC-treated silica | Neodymium neodecanoate on DEAC-treated silica |
| Cocatalyst | 10% DIBAH in isopentane | 10% DIBAH in isopentane | 10% TIBA in isopentane |
| PROCESS CONDITIONS | | | |
| Reaction Temperature (° C.) | 60 | 60 | 65 |
| Monomer partial pressure (psia) | 63 | 63 | 35 |
| Polymer produced (lb) | 5 | 4 | |
| Reaction time | 1 hr 45 min | 1 hr 35 min | 4 |
| PRODUCT ANALYSIS | | | |
| % Carbon Black N-650 by analysis | 36 | 39 | 40 |
| Average particle size by sieve analysis (inch) | 0.027 | 0.030 | |
| Cocatalyst/Catalyst Feed ratio* | 28 | 29 | |
| Neodymium content in the polymer (ppm) | 150 | 200 | |
| Reduced Viscosity (dl/g) | 4.2 | 3.7 | |
| Mooney viscosity (est. gum) ML (1 + 4 @ 100° C.) | 62 | 39 | |
| % cis-1,4 | 95.5 | 95.6 | |

*molar ratio of Al to rare earth metal in continuous feeds

EXAMPLE 30

In an example of the process of the invention a fluidized bed reaction system as described above, is operated as described below to produce polybutadiene. The polymer is produced under the following reaction conditions: 60° C. reactor temperature and 120 psia total reactor pressure. The partial pressure of the butadiene monomer inside the reactor is 96 psia. The partial pressure of nitrogen is 24 psia. The catalyst system employed in this Example is neodymium neodecanoate supported on DEAC-treated silica with tri-isobutylaluminum as co-catalyst. Catalyst and co-catalyst feeds are adjusted to give a 60:1 molar ratio of Al to Nd. At steady state the monomer is fed into the reaction system at the rate of 46.2 lb/h. Dried N-650 carbon black is fed to the reactor at the rate of 20 lb/h. Butadiene monomer leaves the reactor at 13 lb/h in vent streams. The production rate is 30 lb/h of polymer after adjusting for the carbon black content. The product has a Mooney viscosity ML (1+4@100° C.) of 55. Other conditions are shown for Example 30 in the table.

At steady state a total of 46.2 lb/h butadiene is being fed to the reactor and a total of 43 lb/h is accounted for leaving the reactor as gas in a vent stream or as polymer. The difference of 3.2 lb/h must be unreacted liquid butadiene monomer in the polymer leaving the reactor. Since the polymer discharged is identical with the polymer in the bed, the polymer in the bed must contain the same proportion of liquid monomer, i.e. there must be 11.9 lbs of dissolved liquid monomer in the 112 lbs polymer bed.

The reactor volume is 55 ft$^3$. At the partial pressure of 96 psia, there are 44.4 lbs of butadiene in the reactor gas-phase. The total unpolymerized butadiene in the reactor is thus 56.3 lbs (=44.4+11.9). If all of this butadiene were in the gas phase of this reactor at once it would have a partial pressure of 125 psia and its condensation temperature would be 69° C. Therefore the reactor at 60° C. is being operated below the condensation temperature of the monomer present in the polymerization zone. Furthermore, the presence of this liquid monomer in the gas-phase reactor does not cause agglomeration of the polymer.

EXAMPLE 31

In another example of the process of the invention the polymerization is conducted as described in Example 30 except that the catalyst is neodymium neodecanoate fed as a solution in hexane. The table gives further details on this example.

EXAMPLE 32

In an example of the process of the invention a fluidized bed reaction system as described above, is operated as described below to produce polyisoprene. The polymer is produced under the following reaction conditions: 65° C. reactor temperature and 100 psia total reactor pressure. The partial pressure of the isoprene monomer inside the reactor is 30 psia. The partial pressure of nitrogen is 70 psia. The catalyst system employed in this Example is neodymium neodecanoate supported on DEAC-treated silica with tri-isobutylaluminum as co-catalyst. Catalyst and co-catalyst feeds are adjusted to give a 60:1 molar ratio of Al to Nd. At steady state the monomer is fed into the reaction system at the rate of 35.4 lb/h. Dried N-650 carbon black is fed to the reactor at the rate of 20 lb/h. Isoprene monomer leaves the reactor at 2 lb/h in vent streams. The production rate is 30 lb/h of polymer after adjusting for the carbon black content. The product has a Mooney viscosity ML (1+4@100° C.) of 55. Other conditions are shown for Example 32 in the table.

At steady state a total of 35.4 lb/h isoprene is being fed to the reactor and a total of 32 lb/h is accounted for leaving the reactor as gas in a vent stream or as polymer. The difference of 3.4 lb/h must be unreacted liquid isoprene monomer in the polymer leaving the reactor. Since the polymer discharged is identical with the polymer in the bed, the polymer in the bed must contain the same proportion of liquid monomer, i.e. there must be 12.7 lbs of dissolved liquid monomer in the 112 lbs polymer bed.

The reactor volume is 55 ft$^3$. At the partial pressure of 30 psia, there are 17.2 lbs of isoprene in the reactor gas-phase. The total unpolymerized isoprene in the reactor is thus 29.9 lbs (=17.2+12.7). If all of this isoprene were in the gas phase of this reactor at once it would have a partial pressure of 54.5 psia and its condensation temperature would be 80° C. Therefore the reactor at 65° C. is being operated below the condensation temperature of the monomer present in the polymerization zone. Furthermore, the presence of this liquid monomer in the gas-phase reactor does not cause agglomeration of the polymer.

EXAMPLE 33

In another example of the process of the invention the polymerization is conducted as described in Example 32 except that the catalyst is neodymium neodecanoate fed as a solution in hexane. The table gives further details on this example.

|  | EXAMPLE NO. | | | |
| --- | --- | --- | --- | --- |
|  | 30 | 31 | 32 | 33 |
|  | PRODUCT: | | | |
|  | POLYBU-TADIENE | POLYBU-TADIENE | POLYISO-PRENE | POLYISO-PRENE |
| Reaction Conditions: | | | | |
| Temperature (° C.) | 60 | 60 | 65 | 65 |
| Total Pressure (psia) | 120 | 120 | 100 | 100 |
| Superficial Velocity (ft/s) | 1.75 | 1.75 | 1.75 | 1.75 |
| Production Rate (lb/h) | 30 | 30 | 30 | 30 |
| Total Reactor Volume (ft$^3$) | 55 | 55 | 55 | 55 |
| Reaction Zone Volume (ft$^3$) | 7.5 | 7.5 | 7.5 | 7.5 |
| Bed Height (ft) | 7.0 | 7.0 | 7.0 | 7.0 |
| Bed Diameter (ft) | 1.17 | 1.17 | 1.17 | 1.17 |
| Bed Weight (lbs) | 112 | 112 | 112 | 112 |
| Cycle Gas Composition (mole %): | | | | |
| N$_2$ | 20 | 20 | 70 | 70 |
| Butadiene | 80 | 80 | — | — |
| Isoprene | — | — | 30 | 30 |
| Catalyst: | Nd Neodec-anoate on DEAC-treated silica | Nd Neodec-anoate in hexane | Nd Neodec-anoate on DEAC-treated silica | Nd Neodec-anoate in hexane |
| Co-catalyst: | TIBA | TIBA | TIBA | TIBA |

-continued

| | EXAMPLE NO. | | | |
|---|---|---|---|---|
| | 30 | 31 | 32 | 33 |
| | | PRODUCT: | | |
| | POLYBU-TADIENE | POLYBU-TADIENE | POLYISO-PRENE | POLYISO-PRENE |
| Monomer Feed Rate (lb/h) | | | | |
| Butadiene | 46.2 | 46.2 | — | — |
| Isoprene | — | — | 35.4 | 35.4 |
| Monomer Vent Rate (lb/hr) | 13 | 13 | 2 | 2 |
| Polymer Composition (wt. %): | | | | |
| Butadiene | 100 | 100 | — | — |
| Isoprene | — | — | 100 | 100 |

EXAMPLE 34

In example 34, the fluid bed reactor of the type generally depicted in the figure is employed. The reactor has a lower section about 3 meters in height and 0.36 meter in diameter and an upper section of about 4.5 meters in height and 0.6 meter in diameter. In example 34, precursor is used to catalyze the reaction. The precursor is made by spray drying a magnesium chloride/titanium chloride/tetrahydrofuran solution with fumed silica. The resulting solid is slurried with Kaydol mineral oil at a concentration of approximately 28 weight percent solids. The precursor is introduced into the polymerization zone using both isopentane and nitrogen as a carrier. The superficial gas velocity is about 0.55 meters per second. Triethylaluminum in a 5% by weight solution of isopentane is also added to the reactor. Mineral oil (Kaydol) is used as the liquid component and is added to the recycle gases immediately prior to their entry into the reaction vessel. The example is summarized below.

| CATALYST: | |
|---|---|
| Titanium, wt. % of solids | 2.47 |
| THF, wt. % of solids | 25 |
| Precursor Solids Concentration, wt % | 28 |
| REACTION CONDITIONS: | |
| Reactor Temp, ° C. | 85 |
| Reactor Pressure, psig | 350 |
| H2/C2 (mol) | 0.009 |
| C6/C2 (mol) | 0.035 |
| C2 partial press., psi | 33 |
| iC5 conc., mole % | 10 |
| Residence time, hr. | 2.6 |
| Catalyst feed rate (cc/hr) | 8.5 |
| Cocatalyst feed rate (cc/hr) | 190 |
| Liquid Comp., wt. % in bed | 9.05 |

EXAMPLES 35 to 37

In the following examples, a fluid bed reactor of the type generally depicted in the figure is employed. The reactor has a lower section about 3 meters in height and 0.33 meter in diameter and an upper section about 4.8 meters in height and 0.6 meter in diameter. In each of the examples, a catalyst is used which is obtained from a precursor made by impregnating a magnesium chloride/titanium chloride/tetrahydrofuran complex onto a triethylaluminum treated silica support. The silica is first dried at 600° C. to remove water and most of the surface silanols, and chemically treated with triethylaluminum to further passivate the remaining silanols. The dried, free-flowing precursor is then further reduced with diethylaluminum chloride in a tetrahydrofuran solution to become the finished catalyst. The catalyst is introduced into the polymerization zone using a nitrogen carrier gas. The superficial gas velocity is about 0.55 meters per second. Triethylaluminum in a 5% by weight solution of isopentane is also added to the reactor.

In example 35, silicon oil (L-45, 500 centistokes, available from OSi Specialty Chemicals Inc., Danbury, Conn., United States of America) is used as the liquid component. In example 36, n-octane is used as the liquid component. In example 37, a solution of 35 weight percent of a $C_{16}$ alpha olefin mixture (about 75% cetene) in mineral oil ("Nujol"). The following table summarizes the experiments.

TABLE

| Example | 35 | 36 | 37 |
|---|---|---|---|
| Catalyst Composition: | | | |
| Titanium (wt. %) | 1.22 | 1.08 | 1.15 |
| DEAC/THF (mol) | 0.6 | 0.2 | 0.4 |
| TnHAl/THF (mol) | 0 | 0.23 | 0.16 |
| Reaction Conditions: | | | |
| Reactor Temp, ° C. | 82 | 68 | 80 |
| Reactor Pres. psia | 315 | 315 | 315 |
| $H_2/C_2$ (mol) | 0.253 | 0.218 | 0.202 |
| $C_6/C_2$ (mol) | 0.073 | 0.075 | 0.0 |
| Liq. Comp., wt. % in bed | 10.23 | 12.53 | 9.27 |
| $C_2$ partial press. psia | 38 | 35 | 32 |
| $N_2$ vol. % | 82 | 81.6 | 87 |
| Residence time, hr. | 3.2 | 3.8 | 3.4 |
| Cocatalyst feed rate (cc/hr) | 135 | 135 | 135 |

In each of the examples, fluidization is maintained and a free-flowing product is obtained. In example 37, cetene is incorporated into the polyethylene polymer. In example 36, approximately a 500 milliliter sample of polymer particles and reaction gases from the bed is withdrawn and the particles are allowed to settle without cooling in the presence of ethylene at a pressure of about 315 psia. The sample exotherms slightly but the particles are not fused and octane is vaporized. The incorporation of hexene in the copolymer of example 36 is slightly higher than that of a similar process but in which no octane is present. In each of the examples, the amount of fines in the product is reduced as compared to similar processes that do not employ the liquid component. This confirms that Liquid Component in the polymerization zone can affect polymer particle morphology.

EXAMPLE 38

A cold model test is conducted to demonstrate the effect of free liquid in a fluidized bed. A gas fluidization system having a volume of 32 cubic feet (907 liters) contains 55 pounds (25 Kg.) of the polymer of example 2. Nitrogen is circulated to achieve the fluidization and the temperature is maintained at about 40° C. To the fluidized mixture is added 9.3 pounds (4.2 Kg.) of octene. At 40° C., the amount of octene required to saturate the fluidization system is 0.34 pounds (155 g) and the amount that could be sorbed by the polymer is about 6.1 pounds (2.75 Kg). Microdroplets of octene circulated throughout the system. The test continued for 5 hours.

EXAMPLES 39 to 43

In these examples, a fluid bed reactor of the type generally depicted in the figure is employed. The reactor has a lower section about 40.5 feet (about 12.3 meters) in height and 12.67 feet (about 3.9 meters) in diameter. A precursor is used to catalyze the reaction. The precursor is made by spray drying a magnesium chloride/titanium chloride/tetrahydrofuran solution with fumed silica and is similar to that used in Example 35. The resulting solid is slurried with Kaydol mineral oil at a concentration of approximately 28 weight percent solids. The precursor is introduced into the polymerization zone using both n-hexane and nitrogen as a carrier. The superficial gas velocity in the reactor is about 0.63 meters per second. Triethylaluminum in a 5% by weight solution of n-hexane is also added to the reactor by injection into the recycle gas stream immediately prior to entry into the reaction vessel. Also, a feed of liquid n-hexane is provided to the recycle gas stream immediately prior to entry into the reactor. This stream is fed at ambient temperature. The amount of n-hexane fed is sufficient to replenish that lost from the polymerization zone such as with discharged polyethylene such that the condensate weight percent in the gases to the reactor is substantially constant. The examples are summarized below.

| Example | 39* | 40 | 41* | 42 | 43 |
|---|---|---|---|---|---|
| Product: | | | | | |
| Density (g/cc) | 0.963 | 0.963 | 0.926 | 0.926 | 0.926 |
| Melt Index | 8.2 | 8.2 | 49 | 48 | 52 |
| Reaction Conditions: | | | | | |
| Temperature, ° C. | 108 | 108 | 89 | 88 | 87 |
| Pressure, psig | 350 | 350 | 350 | 350 | 350 |
| $C_2$ Pressure, psia | 178 | 175 | 108 | 111 | 110 |
| Comonomer | | | Butene | Butene | Butene |
| $C_4/C_2$ | | | 0.32 | 0.32 | 0.32 |
| $H_2/C_2$ | 0.33 | 0.32 | 0.80 | 0.79 | 0.79 |
| Catalyst Productivity, lbs product/lb catalyst | 4960 | 5630 | 2960 | 3220 | 3990 |
| Liquid Component | n-hexane | n-hexane | n-hexane | n-hexane | n-hexane |
| Reactor Inlet Temp., ° C. | 64 | 85 | 49 | 65 | 65 |
| Cycle gas density, lb/ft³ | 1.23 | 1.78 | 1.38 | 1.64 | 1.74 |
| Ethylene, mole % | 49 | 49 | 30 | 30 | 30 |
| Nitrogen, mole % | 15.4 | 10.6 | 22.9 | 20.8 | 19.1 |
| Butene-1, mole % | | | 9.6 | 9.7 | 9.7 |
| Hydrogen, mole % | 16 | 16 | 24 | 24 | 24 |
| Condensed liquid in cycle gases at reactor inlet, wt. % | 0 | 21.5 | 0 | 17.9 | 23.9 |
| Calculated dew point, ° C. | −35 | 108 | 22 | 89 | 95 |
| Production rate, lbs/hr | 30100 | 53600 | 31600 | 47000 | 49700 |

*Comparative example

Examples 39 to 43 demonstrate the increased productivity of the reactor as the dew point is reached. Note in examples 42 and 43 that the dew point calculation exceeds the actual operating temperature. In actuality, the dew point is the operating temperature of the polymerization zone and the condensed hexane is in the liquid phase. The hexane absorbed in the polymer does not enter into the dew point calculations. In examples 42 and 43, some carry over liquid hexane is in the gases at the reactor outlet. Based upon mass balances around the reactor, in example 42, about 0.5 to 0.7 weight percent liquid is contained in the gases leaving the reactor, and in example 43, about 5 to 8 weight percent liquid are contained in the gases.

We claim:

1. A process for producing polymer by the reaction of one or more monomers in a fluidized bed reaction vessel having a polymerization zone containing a bed of growing polymer particles which comprises:
   a) continuously or intermittently introducing the one or more monomers into said polymerization zone;
   b) continuously or intermittently introducing at least one polymerization catalyst into said polymerization zone;
   c) providing at least one liquid component in the polymerization zone, said liquid component capable of being in the liquid phase in the polymerization zone in an amount sufficient to substantially eliminate the generation of static in the polymerization zone;
   d) continuously or intermittently withdrawing polymer product from said polymerization zone;
   e) continuously withdrawing gases from the polymerization zone, compressing and cooling said gases for recycle to the polymerization zone; and
   f) continuously maintaining sufficient gas flow through the polymerization zone to maintain the bed fluidized, said gas flow comprising recycle of gases withdrawn from the polymerization zone.

2. The process of claim 1 wherein at least a portion of at least one liquid component is introduced above the polymer bed.

3. The process of claim 1 wherein at least a portion of at least one liquid component contacts the walls of the reaction vessel surrounding the polymerization zone.

4. A process for producing polymer by the reaction of one or more monomers in a fluidized bed reaction vessel having a polymerization zone containing a bed of growing polymer particles and a velocity reduction zone above the polymerization zone which comprises:
   a) continuously or intermittently introducing the one or more monomers into said polymerization zone;
   b) continuously or intermittently introducing at least one polymerization catalyst into said polymerization zone;
   c) providing at least one liquid component in the polymerization zone in an amount greater than that which can be absorbed by the polymer particles, and maintaining the polymerization zone under conditions such that the average bulk temperature is at or below the practical dew point;
   d) continuously or intermittently withdrawing polymer product from said polymerization zone;
   e) continuously withdrawing gases from the polymerization zone, compressing and cooling said gases for recycle to the polymerization zone; and
   f) continuously maintaining sufficient gas flow through the polymerization zone to maintain the bed fluidized, said gas flow comprising recycle of gases withdrawn from the polymerization zone
wherein Liquid Component contacts the surfaces of the velocity reduction zone.

5. The process of claim 4 wherein the polymer is a polyolefin.

6. The process of claim 5 wherein at least one monomer is ethylene, propylene, butene-1, isobutene, 1,3-butadiene or isoprene.

7. The process of claim 5 wherein the gases withdrawn from the polymerization zone contain at least a portion of the at least one liquid component in the liquid phase.

8. The process of claim 6 wherein the liquid component is provided in an amount equal to at least 1 percent to about 40 weight percent based on the weight of the bed.

9. The process of claim 4 wherein the liquid phase of the liquid component in the gases withdrawn from the polymerization zone forms a fog.

10. The process of claim 6 wherein the polyolefin is a copolymer of ethylene, and one or more comonomers are contained in the liquid component.

11. The process of claim 10 wherein said comonomers are alpha olefins having between about 12 and 40 carbon atoms.

12. The process of claim 11 wherein at least one monomer is primarily liquid under the conditions in polymerization zone and at least one monomer is primarily gaseous under the conditions in polymerization zone.

13. The process of claim 4 wherein at least a portion of at least one liquid component is introduced about the polymer bed.

14. The process of claim 13 wherein at least a portion of at least one liquid component contacts the interior walls of the reaction vessel surrounding the polymerization zone.

* * * * *